US 9,943,431 B2

(12) United States Patent
Chang et al.

(10) Patent No.: US 9,943,431 B2
(45) Date of Patent: Apr. 17, 2018

(54) ORTHOPEDIC DEVICE

(75) Inventors: Julia Chang, Los Angeles, CA (US); William Arnold, Woodland Hills, CA (US)

(73) Assignee: OSSUR HF, Reykjavik (IS)

( * ) Notice: Subject to any disclaimer, the term of this patent is extended or adjusted under 35 U.S.C. 154(b) by 1025 days.

(21) Appl. No.: 13/090,383

(22) Filed: Apr. 20, 2011

(65) Prior Publication Data

US 2011/0196275 A1    Aug. 11, 2011

Related U.S. Application Data

(63) Continuation of application No. 12/153,390, filed on May 19, 2008.

(60) Provisional application No. 60/996,917, filed on Dec. 11, 2007, provisional application No. 60/924,571, filed on May 21, 2007.

(51) Int. Cl.
*A61F 5/00* (2006.01)
*A61F 5/01* (2006.01)

(52) U.S. Cl.
CPC .................... *A61F 5/0111* (2013.01)

(58) Field of Classification Search
CPC .......... A61F 5/0111; A61F 5/013; A61F 5/01; A61F 5/0585; A61F 5/05841; A61F 5/058; A61F 5/05825; A61F 5/05; A61F 5/04; A61F 5/0113; A61F 5/0127; A61F 13/04; A61F 13/048
USPC .......... 602/28, 27, 6, 7, 8; 128/882
See application file for complete search history.

(56) References Cited

U.S. PATENT DOCUMENTS

| | | | |
|---|---|---|---|
| 4,057,056 A | 11/1977 | Payton | |
| 4,186,738 A | 2/1980 | Schleicher et al. | |
| 4,323,058 A | 4/1982 | Detty | |
| 4,505,269 A | 3/1985 | Davies et al. | |
| 4,559,934 A | 12/1985 | Philipp | |
| 5,219,324 A | 6/1993 | Hall | |
| 5,226,875 A * | 7/1993 | Johnson | 602/27 |
| 5,257,969 A | 11/1993 | Mance | |
| 5,367,789 A | 11/1994 | Lamont | |
| 5,368,551 A | 11/1994 | Zuckerman | |
| 5,429,588 A | 7/1995 | Young et al. | |
| 5,503,622 A | 4/1996 | Wehr | |
| 5,507,720 A | 4/1996 | Lampropoulos | |
| 5,577,998 A | 11/1996 | Johnson et al. | |
| 5,609,568 A | 3/1997 | Andrews | |
| 5,718,673 A | 2/1998 | Shipstead | |
| 5,776,090 A | 7/1998 | Bergmann et al. | |
| 5,827,210 A | 10/1998 | Antar et al. | |
| 5,857,987 A | 1/1999 | Habermeyer | |
| 5,865,779 A | 2/1999 | Gleason | |
| 5,897,520 A | 4/1999 | Gerig | |

(Continued)

*Primary Examiner* — Victoria J Hicks
(74) *Attorney, Agent, or Firm* — Workman Nydegger

(57) ABSTRACT

An orthopedic device as in a dorsal splint for treating plantar fasciitis includes a substantially rigid splint member having an overmolded flexible edge and living hinges, or substantially rigid component pieces received in a flexible member, to provide improved and more comfortable fitting to a user and reduced storage requirements. The splint member is shaped and configured to engage the dorsal aspects of a user's lower leg, ankle, and foot. A soft-good strap system is provided to maintain the dorsal splint in position and has suitable padding to treat various foot conditions.

15 Claims, 13 Drawing Sheets

(56) References Cited

U.S. PATENT DOCUMENTS

| | | | |
|---|---|---|---|
| 5,951,504 A * | 9/1999 | Iglesias | A61F 5/0111 602/16 |
| 6,019,741 A | 2/2000 | Prieskorn | |
| 6,022,331 A * | 2/2000 | Darcey | A61F 5/0111 602/12 |
| 6,024,712 A | 2/2000 | Iglesias et al. | |
| 6,083,185 A | 7/2000 | Lamont | |
| 6,267,742 B1 | 7/2001 | Krivosha et al. | |
| 6,582,382 B2 | 6/2003 | Domanski et al. | |
| 6,648,843 B1 | 11/2003 | Marciano et al. | |
| 6,652,474 B1 | 11/2003 | Quinn et al. | |
| 6,755,798 B2 | 6/2004 | McCarthy et al. | |
| 7,125,392 B2 | 10/2006 | Scott | |
| 7,267,656 B2 | 9/2007 | Cooper | |
| 7,384,584 B2 | 6/2008 | Jerome et al. | |
| 7,488,349 B2 | 2/2009 | Einarsson | |
| 2002/0115950 A1 | 8/2002 | Domanski et al. | |
| 2002/0188239 A1 | 12/2002 | Turtzo | |
| 2003/0204157 A1 | 10/2003 | Cropper | |
| 2004/0019307 A1 | 1/2004 | Grim et al. | |
| 2004/0176714 A1 * | 9/2004 | Darcey | A61F 5/05866 602/21 |
| 2004/0181181 A1 | 9/2004 | Slautterback et al. | |
| 2004/0215123 A1 | 10/2004 | Slautterback et al. | |
| 2004/0225241 A1 * | 11/2004 | Scheinberg | A61F 5/0111 602/5 |
| 2004/0236259 A1 | 11/2004 | Pressman et al. | |
| 2005/0038365 A1 | 2/2005 | Scott | |
| 2006/0052734 A1 | 3/2006 | Evans et al. | |
| 2006/0178606 A1 | 8/2006 | Logue et al. | |

\* cited by examiner

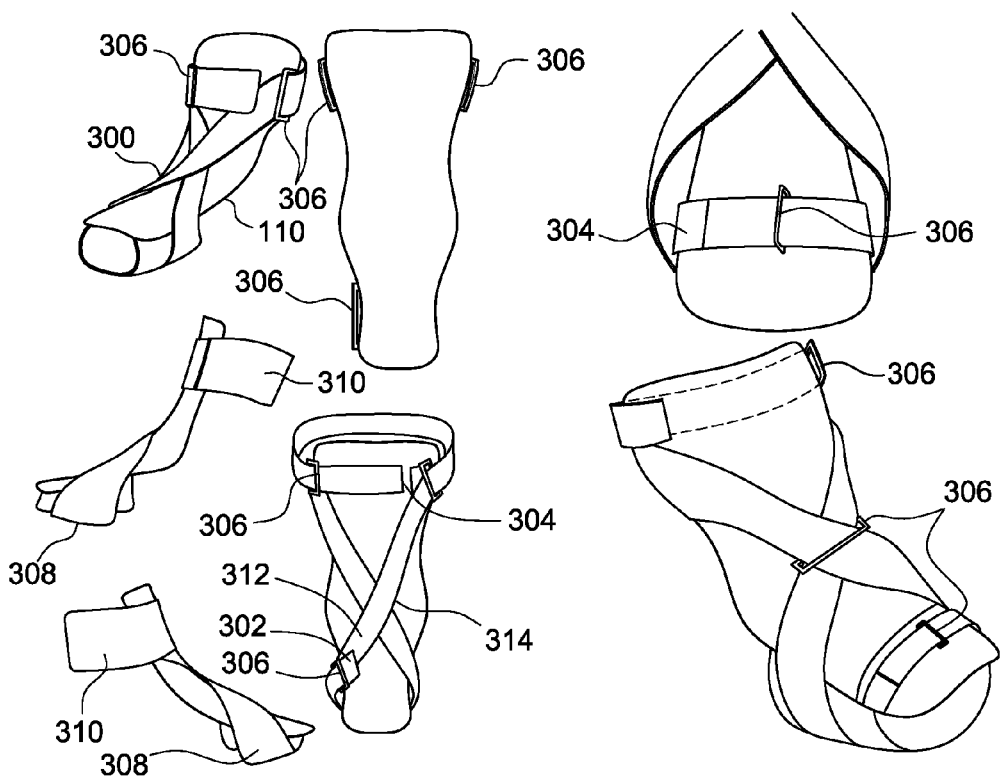
FIG. 3A
FIG. 3B
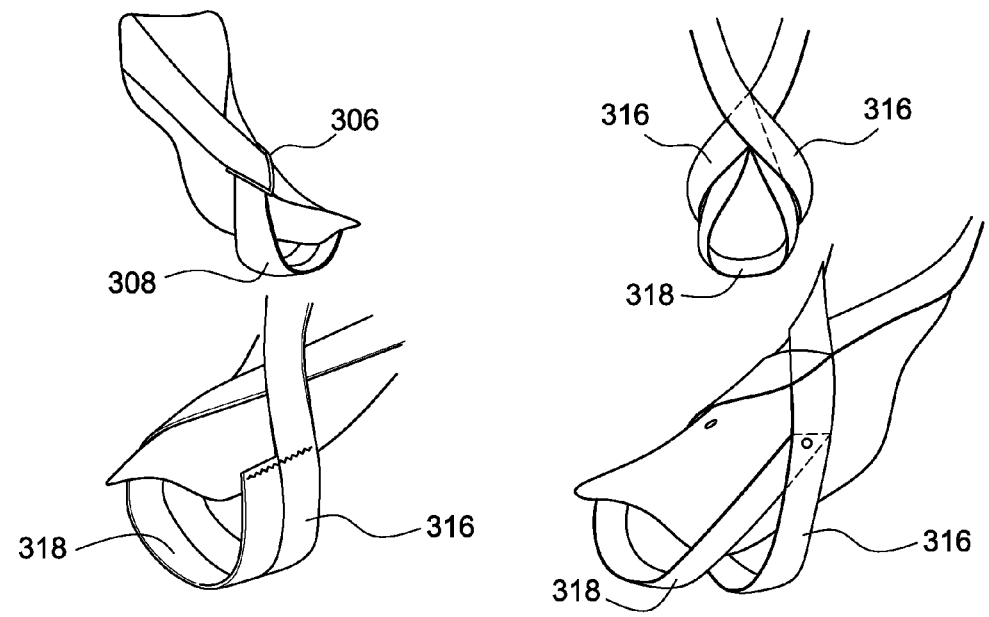
FIG. 3C
FIG. 3D

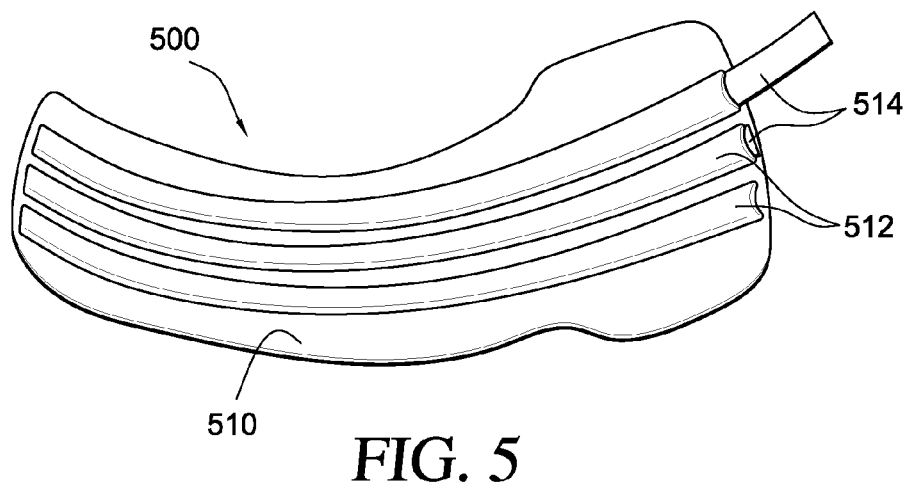
FIG. 5
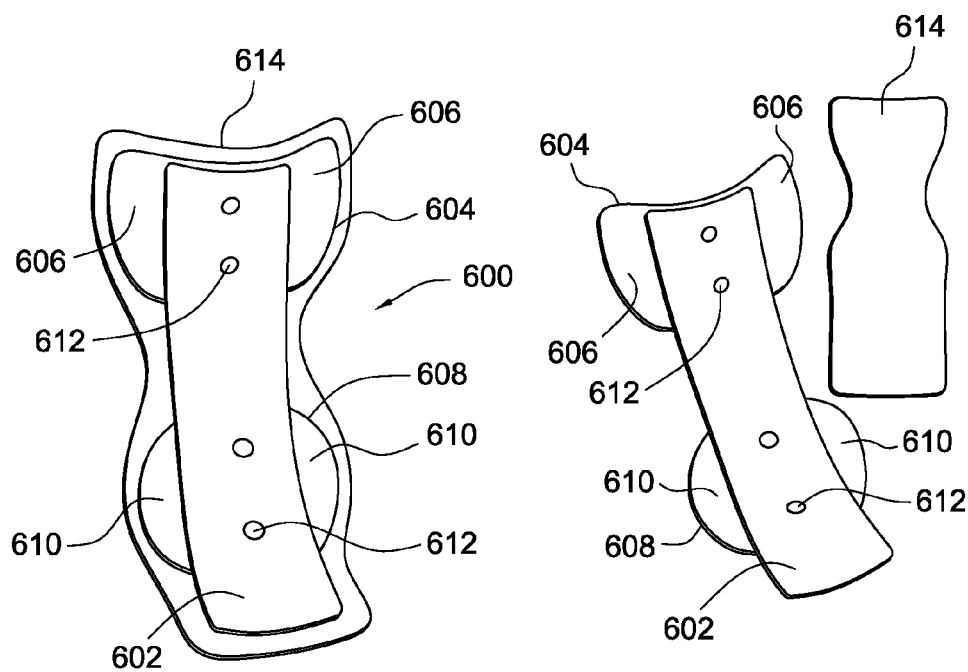
FIG. 6A
FIG. 6B

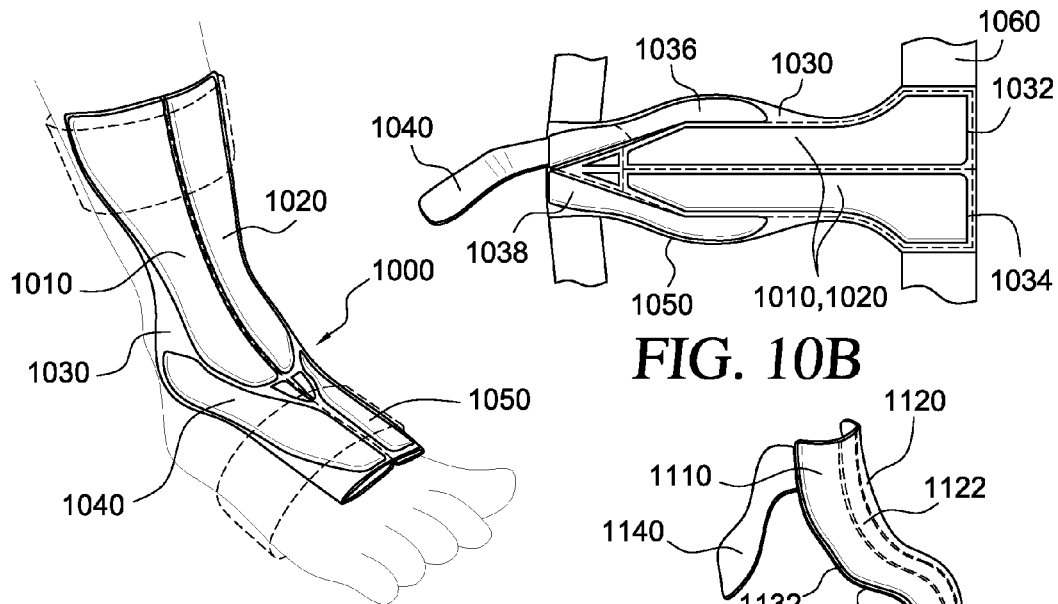
FIG. 10A
FIG. 10B
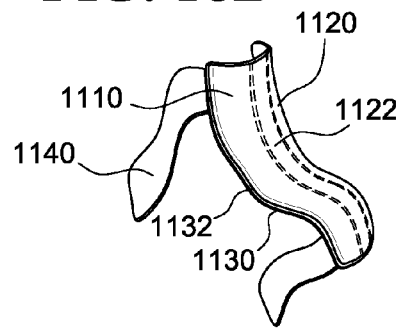
FIG. 11
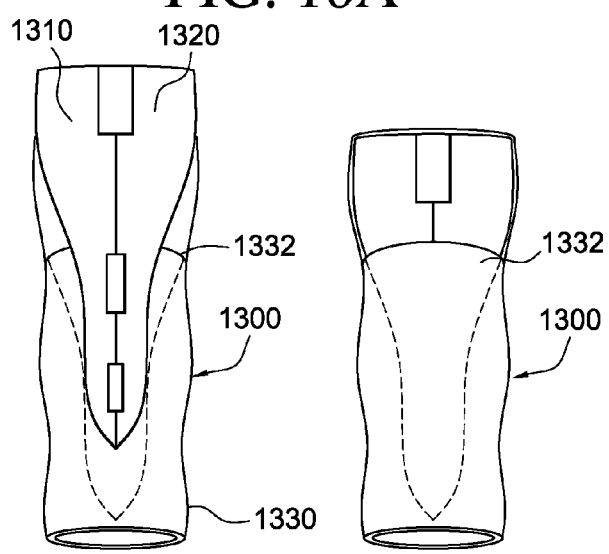
FIG. 13A   FIG. 13B
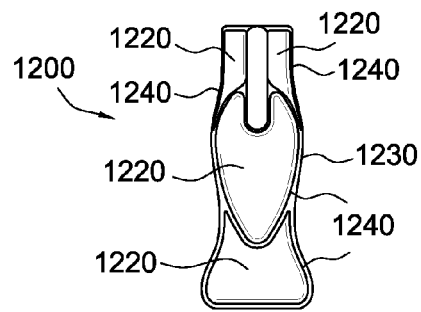
FIG. 12
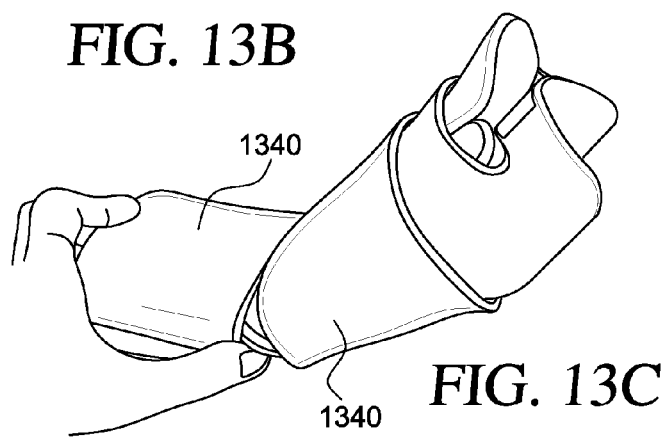
FIG. 13C

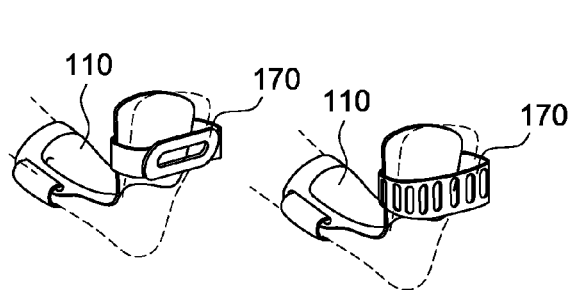
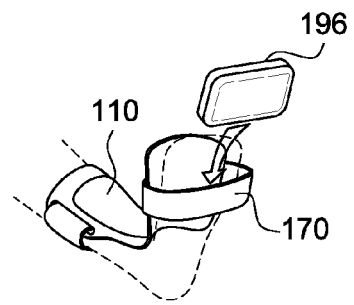
FIG. 14  FIG. 15
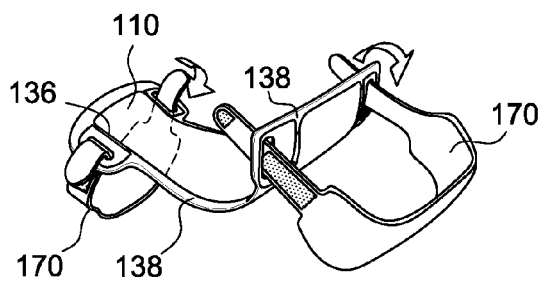
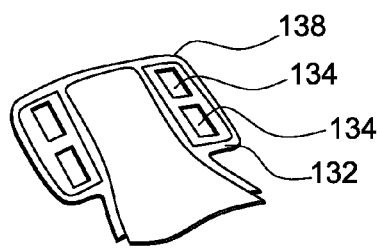
FIG. 16  FIG. 17A
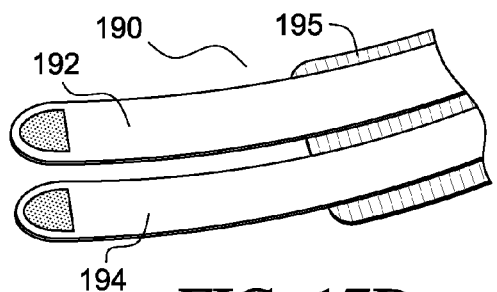
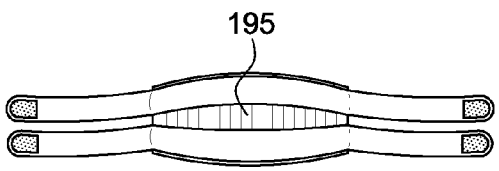
FIG. 17B  FIG. 17C
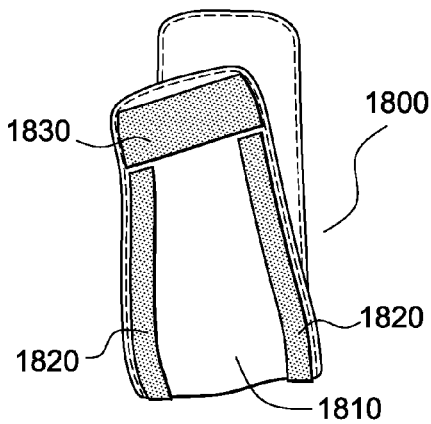
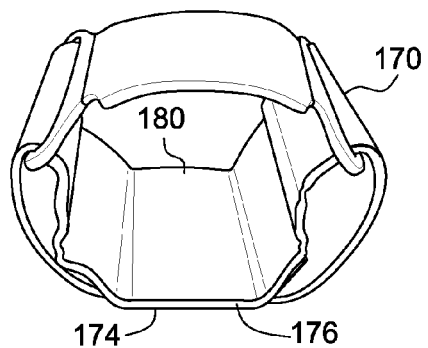
FIG. 18  FIG. 19

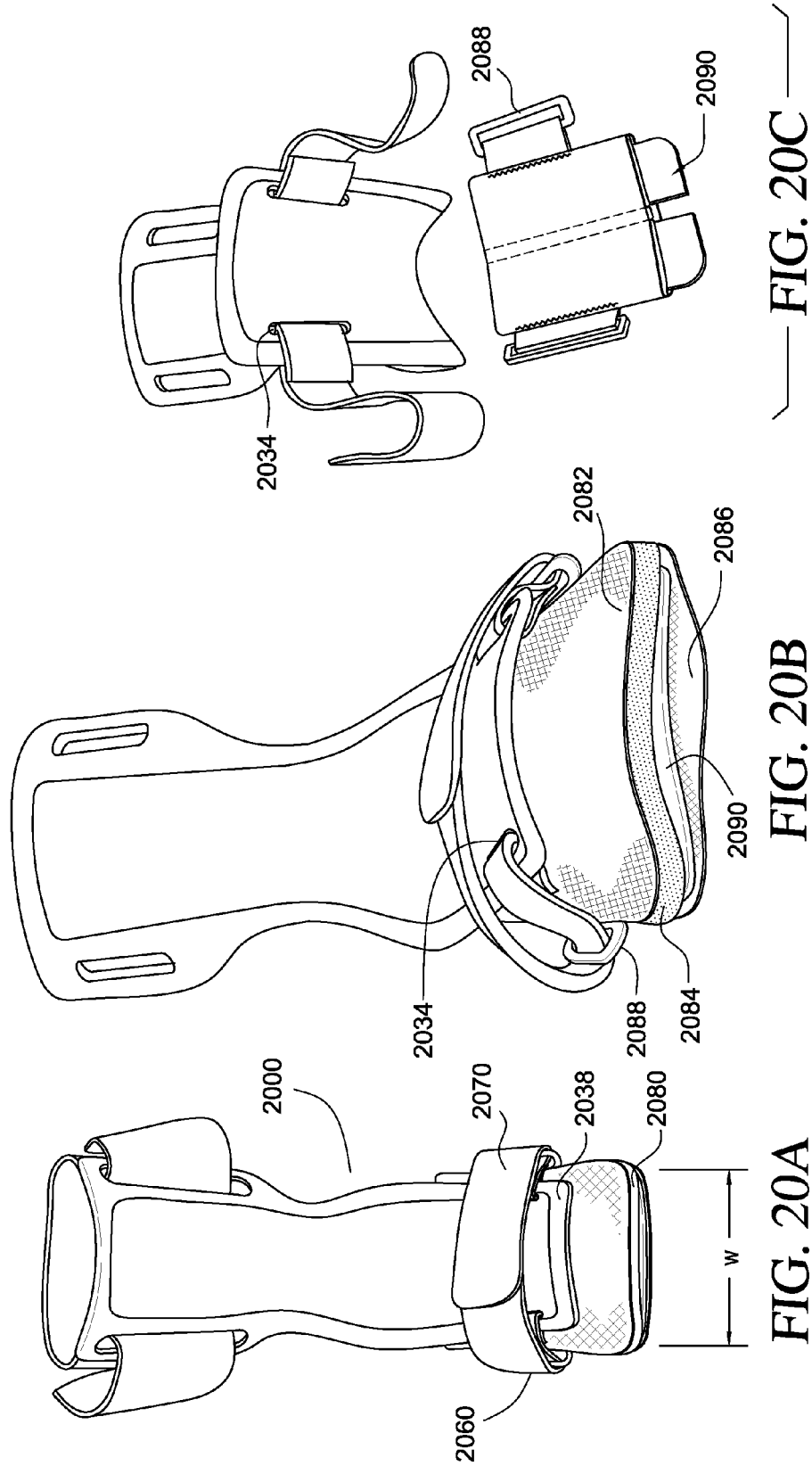

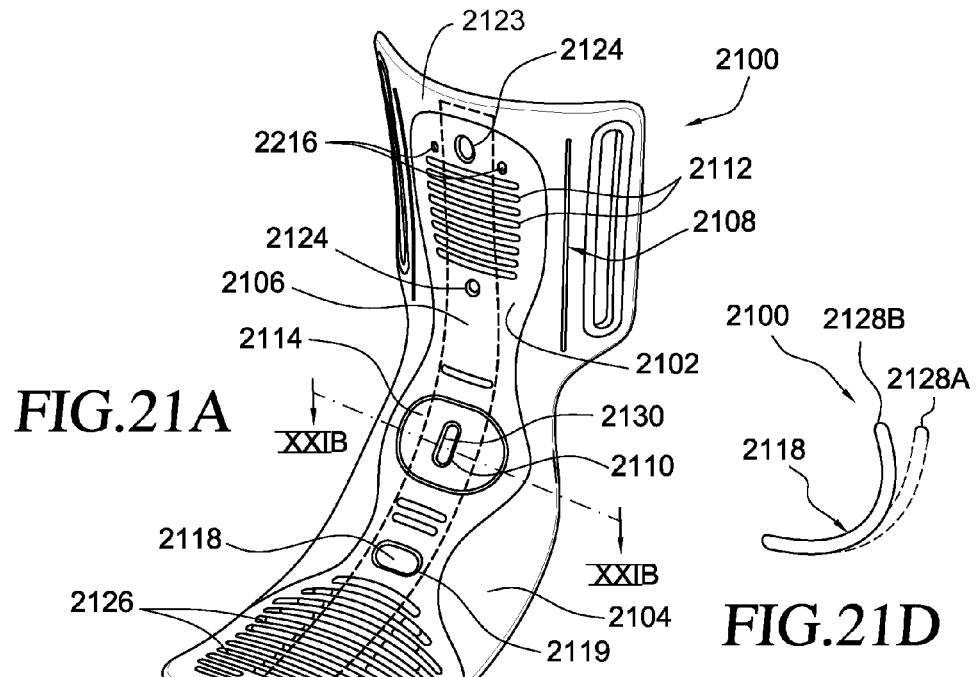
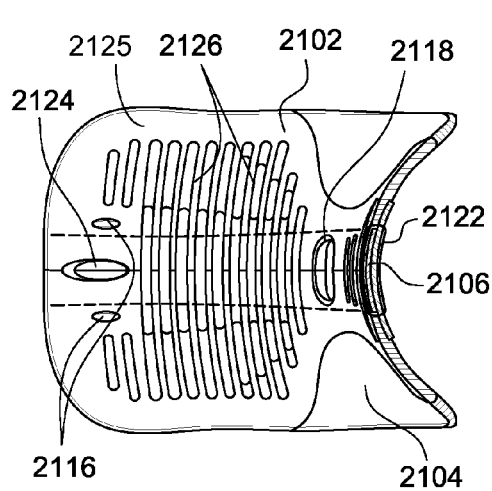
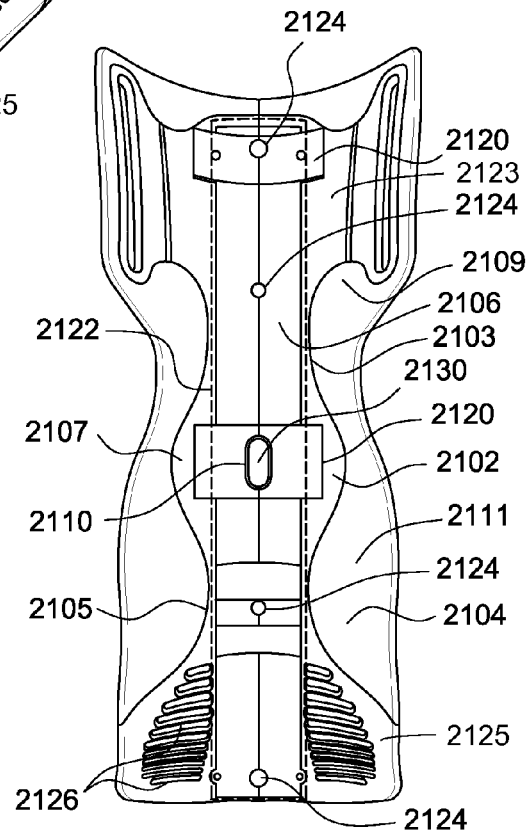

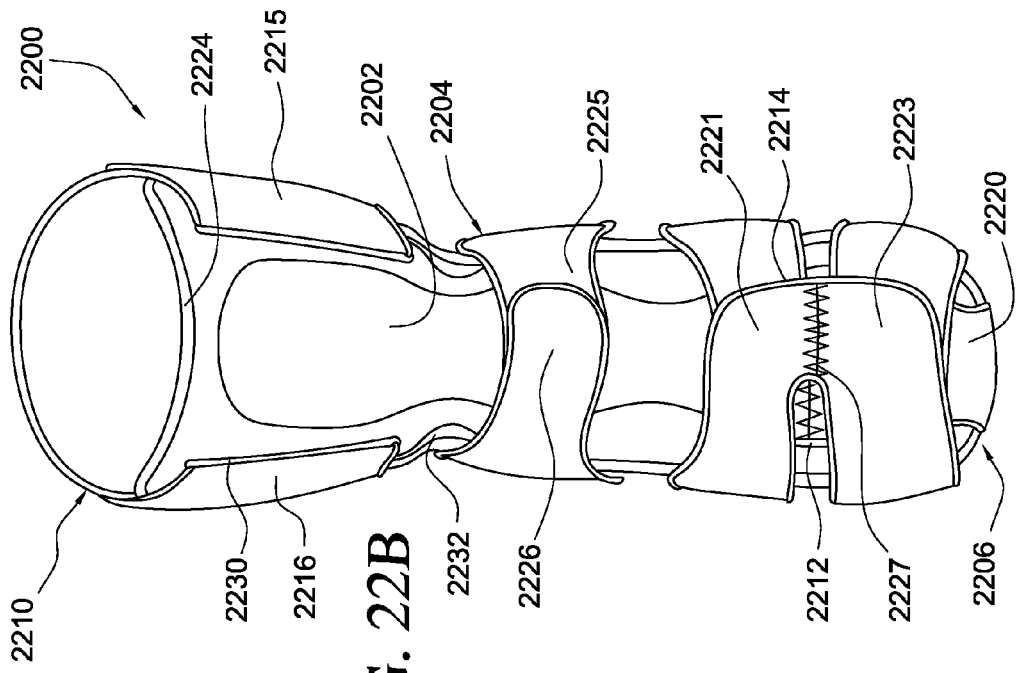
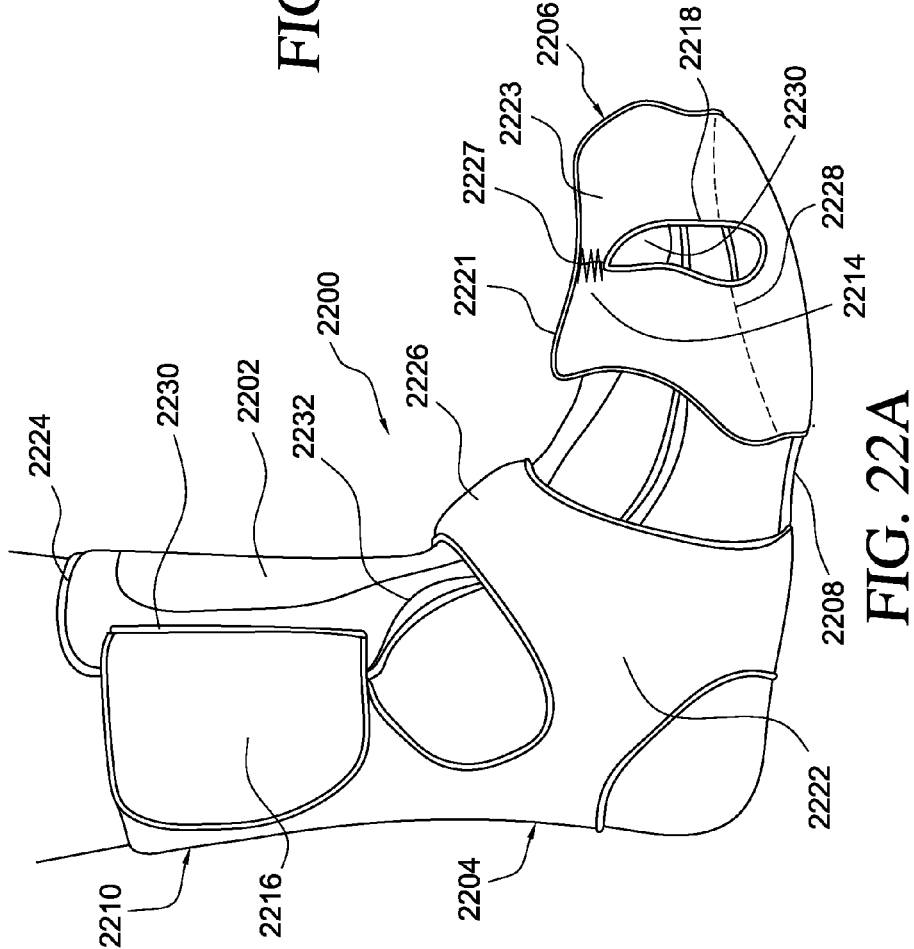

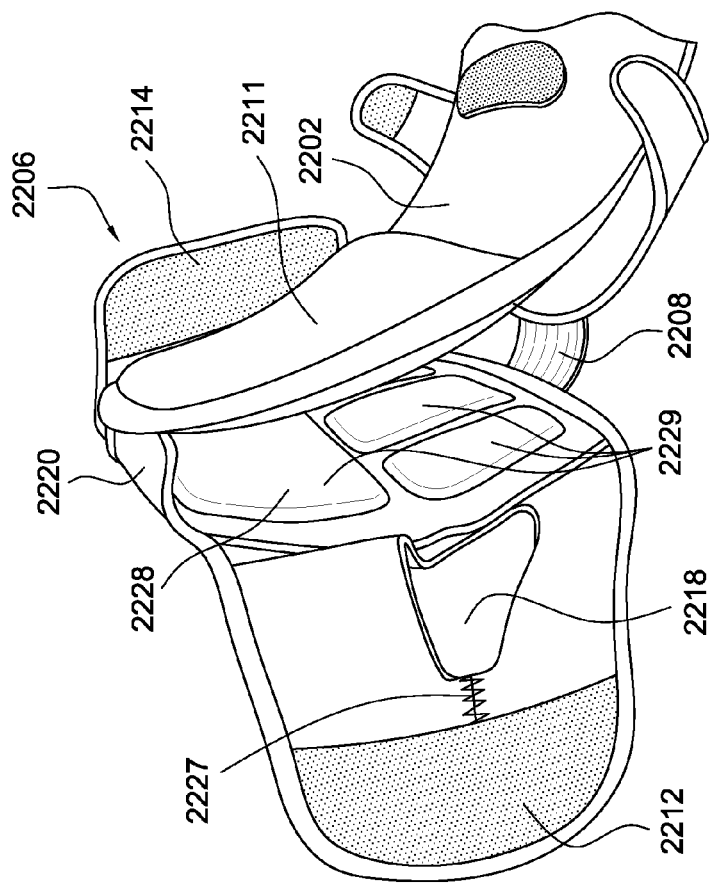
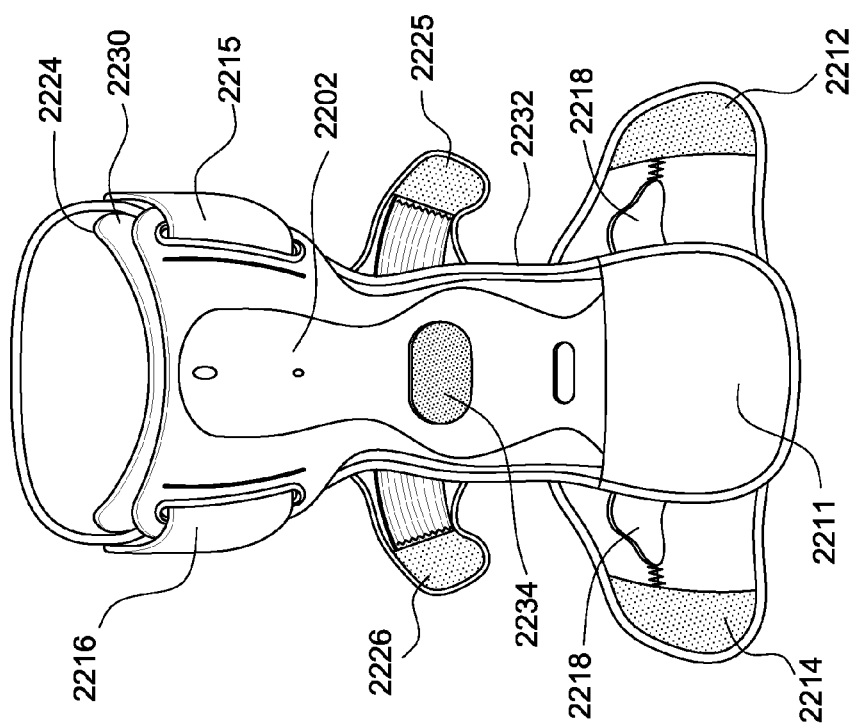
FIG. 22D
FIG. 22C

ORTHOPEDIC DEVICE

CROSS-REFERENCE TO RELATED APPLICATIONS

This application is a continuation of U.S. application Ser. No. 12/153,390 filed on May 19, 2008, which claims the benefit of priority from U.S. provisional application Ser. No. 60/924,571 filed on May 21, 2007, and U.S. provisional application Ser. No. 60/996,917 filed on Dec. 11, 2007.

FIELD OF THE INVENTION

The present invention relates generally to the field of prosthetic and orthopedic devices and more particularly to a dorsal splint for use at night to treat plantar fasciitis and other foot and heel related disorders.

BACKGROUND

Plantar fasciitis is a common problem among people who are active in sports, particularly runners. It is also a prevalent problem for overweight/obese patients and people who remain standing for long periods of time. It is an inflammation of the plantar fascia, the thick tendon on the bottom of the foot which is attached to the heel bone (the calcaneus) and fans forwardly to the toes. The plantar fascia maintains the arch of the foot and is placed in tension during walking and running Any sport where the foot lands repeatedly, such as running or jogging, can overload the plantar fascia and produce an inflammation, usually at the point where the fascia is attached to the heel bone. The reaction of the heel bone to the inflammation is often to produce spike-like projections of new bone called heel spurs. Both the initial inflammation of the fascia and walking on the heel spurs can cause sharp pain.

A broad range of treatments are prescribed for plantar fasciitis, depending upon the severity of the injury and length of time the condition has existed. Among the commonly used treatments are rest, ice, anti-inflammatory/analgesic medication, heel pads, taping, physical therapy and surgery.

Another form of treatment for the condition is the wearing of a splint or orthosis which maintains the foot in a slightly dorsiflexed condition, so that the plantar fascia is maintained in a neutral (90 degree) or a stretched (below 90 degree) position. Typically, such a splint is prescribed for wear at night while the patient is in bed. This maintains a slight stretch of the fascia when it would otherwise be allowed to shorten while the leg and foot muscles are relaxed during sleep. These so-called "night splints" have taken the following forms.

A first type of a night splint consists of a thick, rigid plastic footbed and a pair of rigid plastic bars extending vertically upward on either side of the footbed. A flexible fabric sheath for encircling the foot and leg is also attached to the foot bed, the sheath being open along its front so that the patient may put on the entire appliance like a boot. The footbed underlies the entirety of the patient's foot, and the bars pass along either side of the ankle and lower leg. Straps are attached to the footbed and the bars, and are fastened around the foot and lower leg respectively to secure the splint in position and so maintain the patient's foot in the proper, slightly flexed orientation. Such splints are quite heavy and bulky, and it is common for patients to complain that they are uncomfortable and interfere with sleep.

A second type of a night splint is a generally L-shaped brace made of a relatively thin layer of molded plastic such as polypropylene. The forward-facing surface of the brace is substantially concave to fit around the rear and sides of the patient's calf, ankle and heel. The bottom portion of the "L" extends forwardly beneath the sole of the foot. These splints generally are lined with padding made from a foam or synthetic pile, and are held in place on the lower leg and foot by means of adjustable straps, typically secured with hook-and-pile fasteners. While such splints are less bulky than the first type of prior art splint, some patients still complain that they are uncomfortable, particularly when worn in bed. The rigid portion of the splint contacts the rear and sides of the heel, ankle and lower leg, and so comes between the patient and the bed mattress during most sleeping postures. The splints may be so uncomfortable that patients cannot get a normal night's rest or may discontinue use of the splint before it has achieved the desired therapeutic result.

A third type of orthopedic device for the treatment of plantar fasciitis is known as a foot sling. The foot sling consists of a wide band of flexible, padded material which encircles the patient's lower leg just below the knee, and a flexible strap which passes beneath the ball of the patient's foot and is secured at its ends to the upper leg band on either side of the leg. The strap is tightened to pull upwardly on the foot and so maintain it in a dorsi-flexed position. The foot sling may be uncomfortable to some patient's since the upper leg band must be tight enough around the leg to prevent it from slipping downward when the strap is tightened.

A fourth type of a night splint consists of a rigid plastic, generally "L" shaped brace configured to fit along the dorsal surfaces of the user's foot, ankle and lower leg (a "dorsal" splint). A cloth cover may be provided over each end of the "L" shape in order to provide some interface between the rigid brace and the user's skin, and straps that encircle the brace as well as the foot, ankle, and lower leg, may be connected to the cloth cover to tighten the brace in position. While this type of brace solves some of the problems associated with the previously discussed devices, there still exist issues of patient comfort, as well as the comfort of any person sharing a bed with the patient wearing such a brace. In order for the brace to properly function, it must be substantially rigid, such that the extending portions of the brace will not closely conform to the user's foot, ankle, and lower leg. Thus the brace will not have a good and secure fit. Further, due to the typical injection molding formation of the brace, the edges of the brace may be sharp and cause irritation. The cloth covers do not provide adequate protection from such irritation, which is further exasperated by the loose fit of the brace, or if the edges are flexible enough to be bent, they may dig into the skin even more. These edges can cause irritation to both the user, and to any person sharing the bed with the user.

Thus, there is a need for a dorsal splint that reduces the irritation to a user due to bulky and heavy braces, loose fitting braces, and braces having edges that can cause points of irritation. Further, there is a need for a more comfortable, better fitting brace. Accordingly, a dorsal splint is provided that has a low profile, is less bulky and is lightweight, provides a good and comfortable fit, and solves other problems associated with previous splint designs.

SUMMARY

Exemplary embodiments of a dorsal splint are provided for treating plantar fasciitis that are lightweight, low profile, provide a better and more comfortable fit, and further reduce or eliminate irritation due to edges causing points of irritation.

One embodiment of a dorsal splint includes a substantially rigid splint member having upper, intermediate, and lower portions shaped and configured to be worn on the dorsal aspects of the lower leg, including the shin, dorsal surface of the ankle, or "dorsum," and the dorsal surface of the foot. A flexible edge overmold made from a compliant or flexible material is provided to encase at least an outer edge of the upper portion, and may be provided to encase the edges of the intermediate and lower portions in any desired configuration.

The flexible edge overmold reduces irritation caused by hard or sharp edges of the substantially rigid splint member and further allows the substantially rigid splint member to at least partially conform to the dorsal aspects of the lower leg. A flexible inner member may be utilized in conjunction with the substantially rigid splint member in order to provide a compliant interface between the dorsal splint and the dorsal aspects of the lower leg.

In an exemplary configuration, the flexible inner member is removably attached to the upper, intermediate and lower portions and has first and second surfaces, and proximal and distal ends. The second surface of the flexible inner member defines at least one padded portion and the first surface of the flexible inner member has a hook receiving material. A pouch having a proximal surface including hook receiving material is formed along the first surface along the distal end of the flexible inner member such that the lower portion is received within the pouch. The posterior surfaces of the intermediate and upper members carry hook material for engaging the hook receiving material of the first surface of the flexible inner member. Suitable strap assemblies may be utilized to retain the dorsal splint on the lower leg.

In a variation, the dorsal splint includes a strap in the form of a "figure 8," such that a single strap defines a loop for tightening around the foot. The "figure 8" strap includes crossing over itself on a proximal surface of the intermediate portion of the substantially rigid splint member, and forming another loop for tightening around the calf. The strap configuration allows for the pulling on one end of the strap to cause both loops to tighten simultaneously.

In another variation, the dorsal splint includes at least one slot formed in each of first and second wings of the upper portion for receiving respective ends of a strap, wherein the flexible edge overmold encompasses the slots.

In a further variation, the distal end of the flexible inner member includes an elastic fabric member secured to a first and second edge along the distal end of the inner flexible member. A distal strap is secured to the distal surface of the elastic fabric member. A proximal strap removably engages the slots in the upper portion and each of the proximal and distal straps may carry both hook material and hook receiving material.

In an alternate configuration, the flexible inner member has first, intermediate, and second layers, wherein the first layer defines a hook receiving material; the intermediate layer is a foam layer; and the second layer encases the intermediate foam layer.

In another variation of the dorsal splint, the flexible edge overmold encases an outer edge of each of the upper, intermediate, and lower portions. At least one slot is formed in first and second wings of the upper portion for receiving respective ends of a strap, and at least one slot is formed in first and second sides of the lower portion for receiving respective ends of a strap. The flexible edge overmold also encompasses the slots.

In a related variation, the lower portion also includes first and second wings having slots formed therein for receiving respective ends of a strap. Similar to the previous variation, the flexible edge overmold encompasses the slots.

In an alternate strap configuration, the distal strap includes a first thickness in a middle portion, and a second thickness near first and second ends, where the first thickness is larger than the second thickness. The straps are pulled from two sides and thus, the dorsal splint will be properly positioned in the middle of the limb, as opposed to tilting to one side or the other when being pulled from a single side only and wrapped around the limb.

In another variation, an inflatable bladder is positioned between the proximal surface of the distal strap and the plantar surface of a foot. The bladder may be used to adjust the amount, or angle, of dorsiflexion provided by the splint.

In another configuration, a pad is positioned between the proximal surface of the distal strap and the plantar surface of a foot. The pad may be any suitable pad, such as a gel pad, and may provide therapeutic relief, such as heating or cooling. Different sized pads may be interchangeably provided to adjust the amount, or angle, of dorsiflexion provided by the splint.

In an alternate configuration, each of the proximal and distal straps includes a first layer of flexible material having a first width and a second layer of non-stretch material having a second width that is less than the first width. In this manner a more comfortably fitting, flexible edge strap is provided.

In another strap variation, each of the proximal and distal straps has a first layer of flexible material having a first width and first and second strips of non-stretch material having a second width that is less than the first width. The first and second strips of non-stretch material are positioned along first and second edges of the straps. In this manner the length of the strap is fixed, however the flexible layer may stretch and conform more closely to provide a more comfortable fit. Each of the proximal and distal straps may also have third and fourth strips of non-stretch material positioned along respective first and second ends of the straps so that the ends of the straps may more easily pass through slots in the dorsal splint.

In another strap variation, each of the proximal and distal straps includes first, intermediate, and second layers, wherein the first and second layers are formed from hook receiving material and are positioned on respective sides of the intermediate layer, and the intermediate layer is a foam layer to provide for a more comfortable, form fitting strap.

In another embodiment, the dorsal splint includes an upper portion shaped and configured to engage the dorsal aspect of the leg. First and second living hinges are positioned along first and second sides of the upper portion from which first and second wing portions extend. The lower portion also includes first and second living hinges positioned along first and second sides of the lower portion from which first and second wing portions extend. The living hinges allow the wing portions to flex about the hinges in order to better conform to the leg of the user. When the dorsal splint is removed from the leg, the living hinges cause the wing portions to spring back to their unflexed positions.

In another configuration, the dorsal splint has a flexible inner member to which the overmold and the substantially rigid splint member are integrally molded.

In an alternate configuration, the dorsal splint includes an upper portion and a lower portion. The upper and lower portions are rotatably connected via an intermediate portion connecting the upper and lower portions in a rotatable manner.

In a further embodiment, the dorsal splint has a flexible member having at least one longitudinal pocket for receiving a substantially rigid splint member.

In another embodiment, the dorsal splint includes a substantially rigid splint member. Compliant or flexible upper and lower wing portions are attached to the substantially rigid splint member at upper and intermediate or lower portions. Thus, the upper and lower wing portions provide a comfortable, conforming fit, while the substantially rigid splint member defines the structural support for the lower leg.

In another embodiment, the dorsal splint comprises a flexible member encasing first and second substantially rigid splint members. Each substantially rigid splint member has an upper portion being shaped and configured to engage the dorsal aspect of the leg and an intermediate portion being shaped and configured to engage the dorsum. The flexible member further includes at least one pocket for receiving a substantially rigid lower splint member being shaped and configured to engage the dorsal surface of the foot.

In another embodiment, the dorsal splint has a flexible member encasing first and second substantially rigid splint members. The flexible member further defines at least one pocket located between the first and second splint members for receiving a substantially rigid third splint member.

The numerous advantages, features and functions of the various embodiments of a dorsal splint will become readily apparent and better understood in view of the following description and accompanying drawings. The following description is not intended to limit the scope of the dorsal splint, but instead merely provides exemplary embodiments for ease of understanding.

BRIEF DESCRIPTION OF THE DRAWINGS

FIGS. 3A-D are various views of embodiments of a "figure 8" strap in use with an embodiment of a dorsal night splint.

FIG. 5 is a side view of another embodiment of a dorsal night splint.

FIGS. 6A-B are various front views of another embodiment of a dorsal night splint.

FIGS. 10A-B are various perspective and front views of another embodiment of a dorsal splint.

FIG. 11 is a front perspective view of another embodiment of a dorsal splint.

FIG. 12 is a front view of another embodiment of a dorsal splint.

FIGS. 13A-C are various front and side perspective views of another embodiment of a dorsal splint.

FIG. 14 is a bottom perspective view of another embodiment of a dorsal splint.

FIG. 15 is a bottom perspective view of another embodiment of a dorsal splint.

FIG. 16 is a bottom perspective view of another embodiment of a dorsal splint.

FIGS. 17A-C are various views of another embodiment of a dorsal splint and an associated strap.

FIG. 18 is a side view of an embodiment of a strap for use with various embodiments of a dorsal splint.

FIG. 19 is a bottom perspective view of an embodiment of a strap for use with various embodiments of a dorsal splint.

FIGS. 20A-C are various views of an alternate strap configuration for use with various embodiments of a dorsal splint.

FIG. 21A is a perspective view of another embodiment of a splint member.

FIG. 21B is sectional view taken along line XXIB-XXIB from FIG. 21A.

FIG. 21C is a posterior view of the embodiment shown in FIG. 21A.

FIG. 21D is a schematic view showing different shape configurations of FIG. 21A.

FIG. 22A is an elevational view showing another embodiment of a splint member having a strapping system.

FIG. 22B is a plan view showing the embodiment of FIG. 22A.

FIG. 22C is a plan view showing the embodiment of FIG. 22A in an open configuration.

FIG. 22D is a detailed schematic view showing the toe portion of FIG. 22C in an open configuration.

Figure 1B:
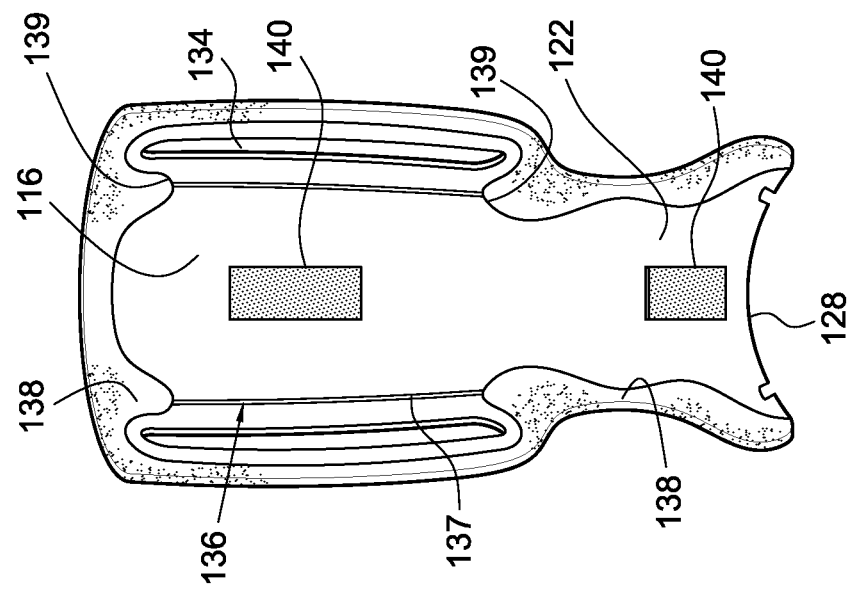
FIG. 1B is a rear view of the embodiment of a dorsal splint shown in FIG. 1A.

In the various figures, similar elements are provided with similar reference numbers. It should be noted that the drawing figures are not necessarily drawn to scale, but instead are drawn to provide a better understanding of the components thereof, and are not intended to be limiting in scope, but rather provide exemplary illustrations.

DETAILED DESCRIPTION OF VARIOUS EMBODIMENTS

A. Environment and Context of the Various Embodiments

The dorsal splint of this disclosure is designed for use by patients while sleeping at night. Of course, the dorsal splint is not limited to being worn at night, but may be worn at any suitable time. For example, any time that a user is sitting down, or otherwise is placing no pressure on the foot, the dorsal splint may be worn.

The dorsal splint is configured and arranged to be worn on either one of the left or right feet, ankles, and lower legs. Accordingly, the description will refrain from describing the dorsal splint with respect to left and right sides, or even lateral and medial sides, since a single dorsal splint may be worn on either the right or left foot. The dorsal splint is to be worn against the dorsal, or top, surfaces of the foot, ankle, and the foreleg, or shin. Any suitable retention mechanism may be used to retain the dorsal splint in proper position on the user.

The dorsal splint is configured to place the foot in dorsiflexion while it is being used by a patient. Thus, the plantar fascia is maintained in a dorsi-flexed position in circumstances where the foot might otherwise naturally tend towards plantarflexion. Accordingly, pain and tearing of the plantar fascia are avoided in situations where the shock of placing the foot in dorsiflexion after prolonged periods of plantarflexion, such as while standing up after a night of sleeping, would otherwise occur.

While not solely limited to use during sleeping, the majority of dorsal splints are worn to bed during the night. Since dorsal splints must be substantially rigid in order to maintain the foot in dorsiflexion, the use of a dorsal splint for prolonged periods of time, for example an eight hour sleeping period, can cause discomfort to the wearer. Additionally, a sleeping partner of the user may also have contact with the dorsal splint, and may also suffer discomfort from rigid surfaces and edges.

A number of embodiments of a dorsal splint are disclosed herein to provide an improved dorsal splint that alleviates or eliminates the above described, and other, shortcomings of the previous splints for treating plantar fascia. These embodiments include improvements in the structure of a dorsal splint and some of the different types of retention mechanisms that may used therewith.

For further ease of understanding the dorsal splint as disclosed herein, a description of a few terms is necessary. As previously stated the term "dorsal" has its ordinary meaning and as used herein refers to the top surfaces of the foot, ankle and foreleg or shin. As used herein, the term "plantar" has its ordinary meaning and refers to a bottom surface, such as the bottom of a foot. As used herein, the term "proximal" has its ordinary meaning and refers to a location that is closer to the heart than another location. Likewise, the term "distal" has its ordinary meaning and refers to a location that is further from the heart than another location. The term "posterior" also has its ordinary meaning and refers to a location that is behind or to the rear of another location. Lastly, the term "anterior" has its ordinary meaning and refers to a location that is ahead of or to the front of another location.

B. Detailed Description of Various Embodiments of a Dorsal Splint

Figure 1A:
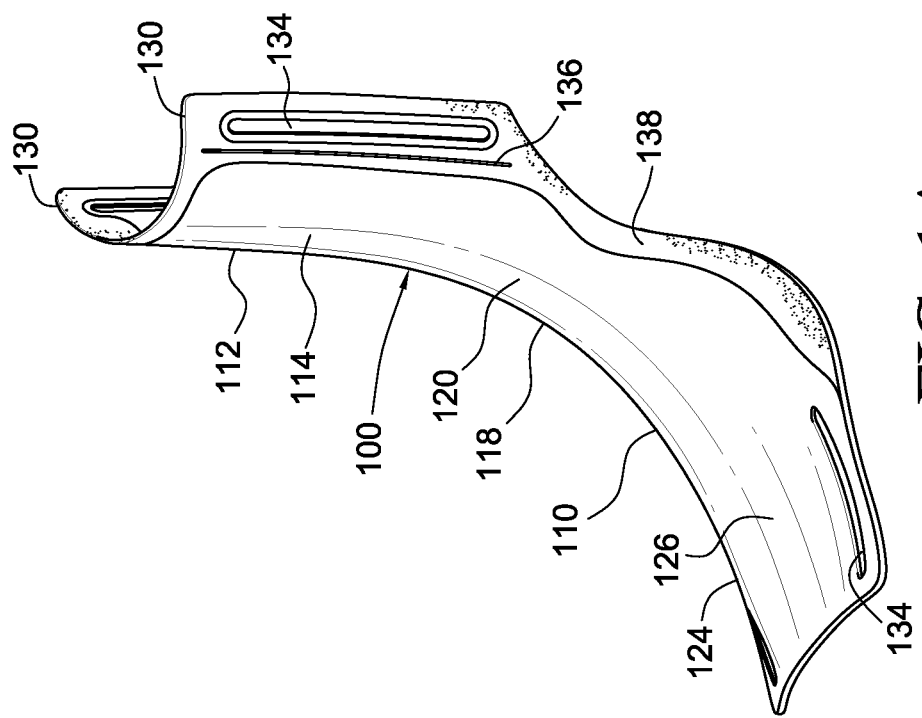
FIG. 1A is a side perspective view of an embodiment of a dorsal splint.

One embodiment of a substantially rigid splint member 110 of a dorsal splint 100 is shown in FIG. 1A. The substantially rigid splint member 110 is shown in a stand-alone manner for ease of illustration. Additionally, the substantially rigid splint member 110 illustrated in FIG. 1A may be used in any number of configurations and embodiments utilizing different padding or retention mechanisms. In order to provide a more comfortable fit, the splint 100 has a flexible edge overmold 138 and living hinges 136 to reduce irritation points and allow the splint 100 to better conform to the user's limb.

Accordingly, the substantially rigid splint member 110 comprises three portions, an upper portion 112, an intermediate portion 118, and a lower portion 124. Each portion is shaped and configured to engage a respective portion of the wearer's body. For example, the upper posterior surface 116 is generally concave in shape to accommodate the fore leg, or shin. The shape of the concavity may be uniform or non-uniform along the posterior surface 116. In order to provide a low profile dorsal splint, the upper anterior surface 114 may have a contoured shape to match the shape of the upper posterior surface 116. The upper portion 112 may have any suitable thickness in order to provide the appropriate rigidity and support to the dorsal splint 100. The thickness may be uniform or non-uniform across the width, and along the length of the upper portion 112.

The upper portion 112 further has anterior 114 and posterior 116 surfaces shaped and configured to engage the dorsal aspect of the leg. The upper portion 112 further includes first and second wing portions 130 extending respectively from first and second sides of the upper portion 112 in order to extend the width of the upper portion 112 so that it may wrap around the dorsal surface of the foreleg.

The intermediate portion 118 is integrally formed with the upper portion 112 and includes anterior 120 and posterior 122 surfaces shaped and configured to engage the dorsum. As an alternative, the intermediate portion 118 may be formed as a separate piece from the upper portion 112. The distinct pieces may be connected to each other in any suitable manner, such as by welding or adhesives.

The intermediate portion 118 is shaped and configured to engage the dorsal aspect of the user's ankle. Accordingly, like the upper portion 112, the posterior surface 122 of the intermediate portion 118 has a substantially concave shape to accommodate the user's ankle. Similarly to the upper portion 112, the shape of the concavity may be uniform or non-uniform.

The width of the intermediate portion 118 may vary along its length in order to provide an appropriate curvature to accommodate the various protrusions of the ankle joint. The thickness of the intermediate portion 118 may also be uniform or non-uniform.

The proximal end of the intermediate portion 118 is merged with the distal end up the upper portion 112 and provides a smooth transition such that a point of irritation is not created at the juncture. Of course, if the intermediate 118 and upper portions 112 are separately formed and joined together, any appropriate surface treatment, such as sanding, grinding, or polishing, may be utilized to provide a smooth transition.

The lower portion 124 is integrally formed with the intermediate portion 118 in order to form a single substantially rigid splint member 110. Proximal 126 and distal 128 surfaces are provided on the lower portion 124. As an alternative, the lower portion 124 may be formed as a separate piece from the intermediate portion 118. The distinct pieces may be connected to each other in any suitable manner, such as by welding or adhesives.

The lower portion 124 is shaped and configured to engage the dorsal aspect of the user's foot. Thus, the distal surface 128 of the lower portion 124 has a substantially concave shape. A flared distal end portion is provided to avoid rigid corners that would dig into the flesh of the dorsal surface of the user's foot. As with the upper 112 and intermediate 118 portions, the concavity and thickness of the lower portion 124 may be uniform or non-uniform.

As shown in FIG. 1A, slots 134 for straps are also provided along either edge of the lower portion 124. The slots 134 may have any suitable length in order to accommodate straps of different sizes. Such slots may also be used to reduce the weight of the substantially rigid splint member 110, even if a strap is not used directly with the slots 134 of the lower portion 124. Of course, if a strap is not to be used directly with slots in the lower portion 124, the slots 134 in the lower portion 124 may not be provided. Whether or not slots 134 are used, the straps are pulled from two sides and thus, the dorsal splint 100 will be properly positioned in the middle of the limb, as opposed to tilting to one side or the other when being pulled from a single side only and wrapped around the limb.

In a similar fashion as discussed above, the proximal end of the lower portion 124 is merged with the distal end of the intermediate portion 118 in order to provide a smooth transition between the two portions.

The combination of the three portions serves to position a user's foot, ankle, and lower leg in a dorsiflexion position. The angle of dorsiflexion may be fixed by the relationship of the three members. Exemplary angles of dorsiflexion may be in the range of 80° to 90°. In particular, a range of 85° to 90° provides a suitable range of dorsiflexion.

The substantially rigid splint member 110 may be formed from any suitable material, for example any appropriate thermoplastic or thermosetting polymer, carbon, carbon fiber epoxy composite, plastic, fiber reinforced plastic, molded chopped fibers, laminates, metal or any other suitable material. Exemplary materials include, but are not limited to, nylons, glass filled nylon, polypropylenes, vinyls, polyvinyl chlorides, high density polyethylene, epoxies, urethanes, and polyesters. The substantially rigid splint member 110 may be formed in any suitable manner, for example injection molding, casting, or curing.

As shown in FIGS. 1A and 1B, "living hinges" 136 are provided in the upper portion 112 between a main a section of the upper portion 112 and the upper wing portions 130 in order to provide flexibility to the wing portions 130 so that the splint 100 may better conform to the user's limb. The living hinge 136 is a thin section of material between the main section of the upper portion 112 and the upper wing portion 130. The living hinge 136 has a thickness that is less than the thickness of the rest of the upper portion 112 or the upper wing portions 130. Since the living hinge 136 has a smaller thickness than the upper portion 112 or the upper wing portions 130, the wing portions 130 and the upper portion 112 are able to flex with respect to each other around the living hinge 136.

The wing portions 130 and the upper portion 112 flex to conform to the user's lower leg via a strap. Thus, a better fit is accomplished between the dorsal splint and the user's leg. When the strap is removed, the wing portions 130 return to their unflexed position due to the action of the living hinges 136 in a manner that will be understood by the skilled artisan.

The specific construction of the living hinge 136 is dependent upon the desired amount of flexing, and the direction of flexing. The actual thickness and shape of the living hinge 136 is dependent upon the thickness of the upper portion 112 and upper wing portions 130. The living hinge 136 may therefore be formed in any suitable shape, size and orientation, in order to provide the desired flexing characteristics.

For example, the living hinge 136 may be provided by a recessed line or groove along the posterior surface 116 of the upper portion 112, and a protruding line or a recessed line or groove along the anterior surface 114 of the upper portion 112. The length of the living hinge 136 may extend substantially along the entire upper portion 112 commensurate in length with the upper wing portions 130. Alternatively, the length of the living hinge 136 may have any suitable length. The actual process of forming the living hinges 136 will be understood by a skilled artisan.

When the dorsal splint 100 is in place on the user's leg, the upper portion 112 is retained in position against the leg, and the upper wing portions 130 are able to flex in order to more closely conform to the user's leg. In this manner, the dorsal splint 100 provides a better fit with the user's leg, and enables a more comfortable fit since the dorsal splint 100 more closely conforms to the shape of the user's leg. The living hinges 136 also aid in preventing the dorsal splint 100 from sliding off of the patient's limb, since the extended upper wing portions 130 that (compared to a single rigid piece) to better conform to the shape of the leg when there is ankle movement.

As illustrated in FIG. 1A, a flexible edge overmold 138 is provided for encasing an outer edge of at least the upper portion 112. The overmold 138 shown in FIG. 1A encases an outer edge of both the upper portion 112 and the intermediate portion 118. The flexible edge overmold 138 may be formed from any suitable material, such as a flexible plastic. Exemplary materials include thermoset polymers, such as solid polyurethane, or thermoplastic elastomers.

In order to provide a low profile brace, the thickness of the overmold 138 may be the same as or smaller than the upper portion 112 or any other portion that the overmold 138 encases the edge of The width of the overmold 138 may be any suitable width so as to provide a compliant interface between the substantially rigid splint member 110 and the user's skin.

In alternative embodiments, such as illustrated in FIG. 1A, slots 134 for receiving straps are provided in the wing portions 130 of the upper portion 112, and along the edges of the lower portion 124. As shown in FIG. 1A, the overmold 138 encompasses the slots 134 in the wing portions 130 of the upper portion 112. Lines of greater thickness may be provided coinciding with the living hinges 136 as a visual reference of the living hinges, or as an aesthetic element. These lines may also be provided in order to prevent cracks from forming in the overmold 138.

The overmold 138 may be formed in situ by injection molding, or by curing in place. In order to aid with retaining the overmold 138 in place, the edge which it encases may have an irregular shape, such as a grooved edge or protruding edge, to provide the material of the overmold 138 a larger surface area for adhesion. Of course, the encompassing of the slots 134 by the overmold 138 also provides a larger surface area for adhesion between the overmold 138 and the portion to which it is connected.

The overmold 138 provides a flexible interface between the rigid edges of the substantially rigid splint member 110 and the user's body. Thus, irritation due to the hard and sometimes sharp edges is reduced or eliminated. Accordingly, the dorsal splint 100 provides a more comfortable fit for the prolonged use during sleeping for both the user and any person sharing the same bed as the user. This feature is an improvement over conventional dorsal splints that do not provide adequate protection from the rigid, and sometimes sharp, edges of the dorsal splints.

As shown in FIG. 1B, the groove or channel 137 defining the living hinges 136 is provided along the posterior surface 116 of the upper member 112. Further, the living hinge 136 defines a recess 139 formed between the wings 134 so as to facilitate bending of the wings 134 relative to the upper portion 112. According to this embodiment, the overmold 138 only partially encompasses the slots 134 on the posterior surface 116 of the upper member 112, in order to keep the recess or groove of the living hinge 136 free of material so that the upper wing portions 130 may more freely flex. This configuration may be used with each embodiment described. Alternatively, although less desirable, the overmold 138 may partially encompass the groove or channel.

Figure 1E:
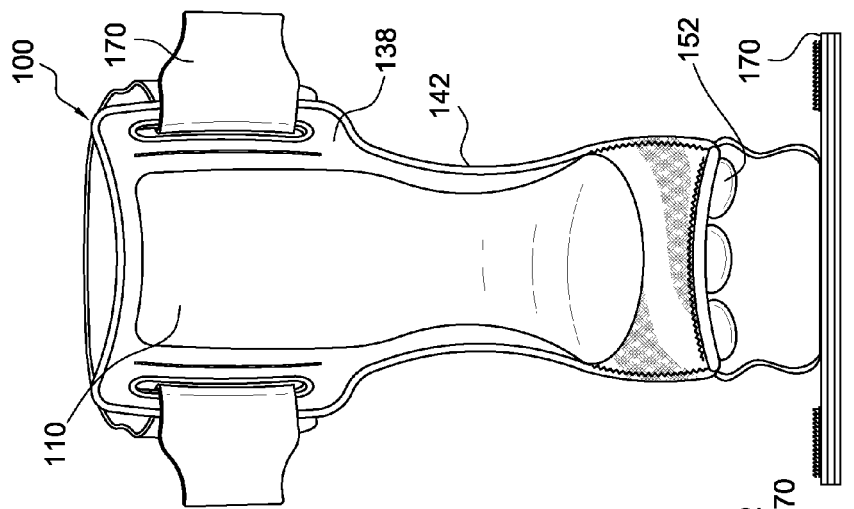
FIG. 1E is a front view of the embodiment of a dorsal splint, similar to that shown in FIG. 1D, and including a proximal strap.
Figure 1D:
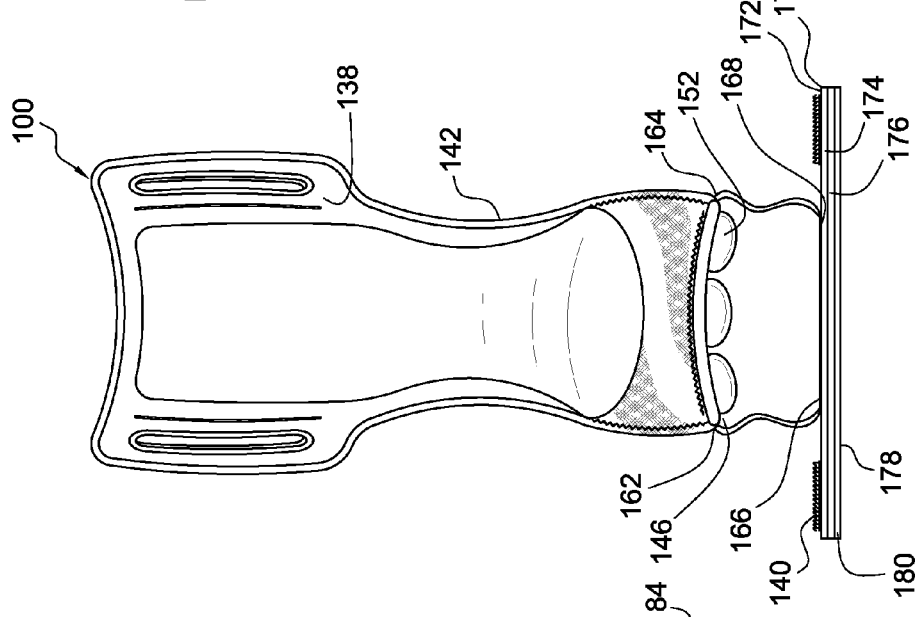
FIG. 1D is a front view of the embodiment of a dorsal splint shown in FIG. 1A including the inner flexible member shown in FIG. 1C.
Figure 1C:
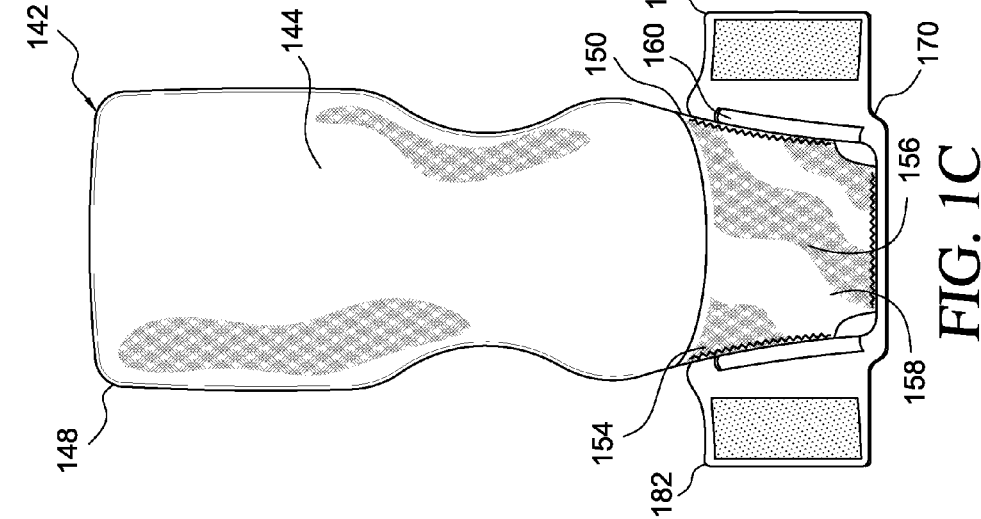
FIG. 1C is a front view of an inner flexible member for use with the embodiment of a dorsal splint shown in FIG. 1A.

As shown in FIG. 1C, fastening mechanisms, such as patches of hook material 140, are provided. The patches are positioned on the posterior surfaces 116, 122 of the upper 112 and intermediate 118 portions to aid with removably retaining a flexible inner member 142 against the posterior surfaces 116, 122 of the upper 112 and intermediate 118 portions, as will be more fully discussed below. Patches 140 may be of any suitable size and may be attached to the posterior surfaces 116, 122 of the upper 112 and intermediate 118 portions in any suitable manner, such as by adhesion.

Alternatively, patches 140 of hook material may be integrally injection molded with the substantially rigid splint member 110. Also, the patches 140 may be of hook receiving material. Further yet, the patches 140 may cover substantially the entire posterior surfaces 116, 122 of the upper 112 and intermediate 118 portions. It will be understood that, any suitable fastening mechanism, such as snap fasteners, may be provided in place of the patches of hook material 140.

As shown in FIG. 1C, the flexible inner member 142 has substantially the same shape as the substantially rigid splint member 110. The flexible inner member 142 acts as a compliant interface between a user's leg, foot, and ankle and the substantially rigid splint member 110. Accordingly, to aid with the reduction of irritation caused by the substantially rigid splint member 110, the flexible inner member 142 may be slightly larger than the substantially rigid splint member 110.

As illustrated in FIGS. 1C and 1D, the flexible inner member 142 has first 144 and second surfaces 146, and proximal 148 and distal 150 ends. The first surface 144 may carry or be made from hook receiving material. Alternatively, the first surface 144 may carry or be made from hook material. The hook receiving material may be broken or unbroken loop material formed by example from nylon. In this manner the first surface 144 is selectively removably fixed to the posterior surfaces 116, 122 of the upper 112 and intermediate 118 portions.

A pouch 154 is provided on the first surface 144 along a portion of the distal end 150 of the flexible inner member 142 for receiving at least a portion of the lower portion 124. The pouch 154 may be formed from any suitable material and may define a proximal surface 156 that carries or is made from hook receiving material 158 for a purpose to be described below. Of course, any suitable fastening material or mechanism, such as hook material or snap fasteners may be provided. In an alternative configuration, the flexible inner member 142 does not include the pouch 154, but instead is retained on the dorsal splint 100 via at least one additional patch of hook material 140 that is positioned on the distal surface of the lower portion 124 in the same manner as discussed above.

In use, the lower portion 124 of the substantially rigid splint member 110 is received within the pouch 154. The flared end portions of the lower portion 124 also help to engage the inner portions of the pouch 154 to assist with maintaining the lower portion 124 within the pouch 154. The first surface of the flexible inner member 142 is then removably fastened to the posterior surfaces 116, 122 of the upper 112 and intermediate 118 portions. Thus the flexible inner member 142 is retained on the substantially rigid splint member 110 so that the dorsal splint 100 may be placed upon the leg, ankle, and foot of the wearer. As an alternative to the pouch 154, further hook and hook receiving materials, or any other suitable fastening mechanism, such as snap fasteners, may be provided. Further, the flexible inner member 142 may be non-removably connected to the substantially rigid splint member 110 by, for example, an adhesive.

The second surface 146 of the flexible inner member 142 includes or defines at least one padding member 152. A plurality of padding members 152 of varying thickness may be provided in any suitable pattern along the second surface 146. For example, a thicker padded portion may be provided in the area of the intermediate portion in order to protect the bony protuberance of the dorsum. Alternatively, thicker padded portions may also be used to increase the angle of dorsiflexion. The padding may be a thermoform pad having a pattern that provides a "formfit." This may be accomplished by utilizing various thicknesses throughout the pattern. The second surface 146 may be a soft covering that is not receptive to receiving hook material. Of course, any suitable material or fabric will suffice.

In order to aid with placing the dorsal splint 100 on the foot of the user, an elastic fabric member 160 is provided. The elastic fabric member 160 has proximal 166 and distal 168 surfaces, as well as first 162 and second 164 ends connected to first and second edges along the distal end 150 of the flexible inner member 142. The elastic fabric member 160 thus forms a loop that the distal portion of the foot is placed within in order to maintain the dorsal splint 100 in position while allowing for further adjustment and tightening.

The ends 162, 164 of the elastic fabric member 160 may be connected to the flexible inner member 142 in any suitable manner, such as by sewing, or by zipper closures. In an alternative embodiment, the elastic fabric member 160 may form a continuous loop that has one surface secured to the second surface 146 of the flexible inner member 142. Accordingly, the elastic fabric member 160 may be an elastic band, or an elastic stockinette, as will be recognized by a skilled artisan.

A distal strap 170 defining proximal 172 and distal 178 surfaces and first 182 and second 184 ends is connected to the distal surface 168 of the elastic fabric member 160. The connection may be such that the strap 170 and elastic fabric member 160 are sewn together around a surface, along multiple lines, or adhesively or otherwise connected.

As best seen in FIGS. 1D, 1E, and 19, the strap 170 includes first 174, intermediate 176, and second 180 layers. The intermediate layer 176 may be an open or closed cell, compressed or thermoformed foam material. Suitable materials include, but are not limited to, polyurethane foams. Thus a strap 170 is provided that includes some cushioning, such that the strap will not dig into the flesh of the user and thus will not cause pain and discomfort. The flexible inner member 142 may be formed in a similar tri-layer manner with the padding 152 being formed in the same manner as the intermediate layer 176 of the strap 170.

The first 174 and second 180 layers define the proximal 172 and distal 178 surfaces. The proximal 172 and distal 178 surfaces may both carry or be composed of hook receiving material. Patches of hook material 140 may also be received along the first 182 and second 184 ends of the strap 170. Of course, as previously discussed, the location of the hook material and the hook receiving material may be interchanged, and other fastening mechanisms, such as buckles or snap fasteners, may be provided.

Once the dorsal splint 100 is located in position on the foot via the elastic fabric member 160, the first 182 and second 184 ends of the strap 170 are folded up and over so that the patches of hook material 140 engage the hook receiving material 158 of the proximal surface 156 of the pouch 154, or the hook receiving material of the strap surfaces 178. In this manner the lower portion 124 are tightened in position along the dorsal surface of the foot. During tightening, the straps are pulled from two sides and thus, the dorsal splint 100 will be properly positioned in the middle of the limb, as opposed to tilting to one side or the other when being pulled from a single side only and wrapped around the limb.

A second, proximal strap 170, as shown in FIG. 1E, secures the upper portion 112 against the lower leg and shin of the user. The proximal strap 170 may have the same construction as previously discussed with respect to the distal strap 170. Each of the first and second ends of the proximal strap 170 are received in respective slots 134 in the upper wing portions 130. The proximal strap 170 extends from the slots 134 between the posterior surface 116 of the upper member 112 and the first surface 144 of the flexible inner member 142 in order to encircle the user's leg. The patches of hook material 140 on the proximal strap 170 are connected directly to the hook receiving material of the surface of the strap 170 to tighten and fasten the proximal strap 170. Of course, any suitable alternate fastening mechanism may be utilized.

Given the above described construction, and in particular the living hinge, overmold, and padded flexible member and straps, the dorsal splint 100 provides an improved and more comfortable fit for both the user and anyone sharing the bed of the user.

Of course, the dorsal splint 100 may be utilized in numerous variations of the above described embodiment. For example, the substantially rigid splint member 110 may be used without the flexible inner member 142, and may instead have proximal and distal straps associated with the slots 134 in the upper and lower portions.

Figure 2A:
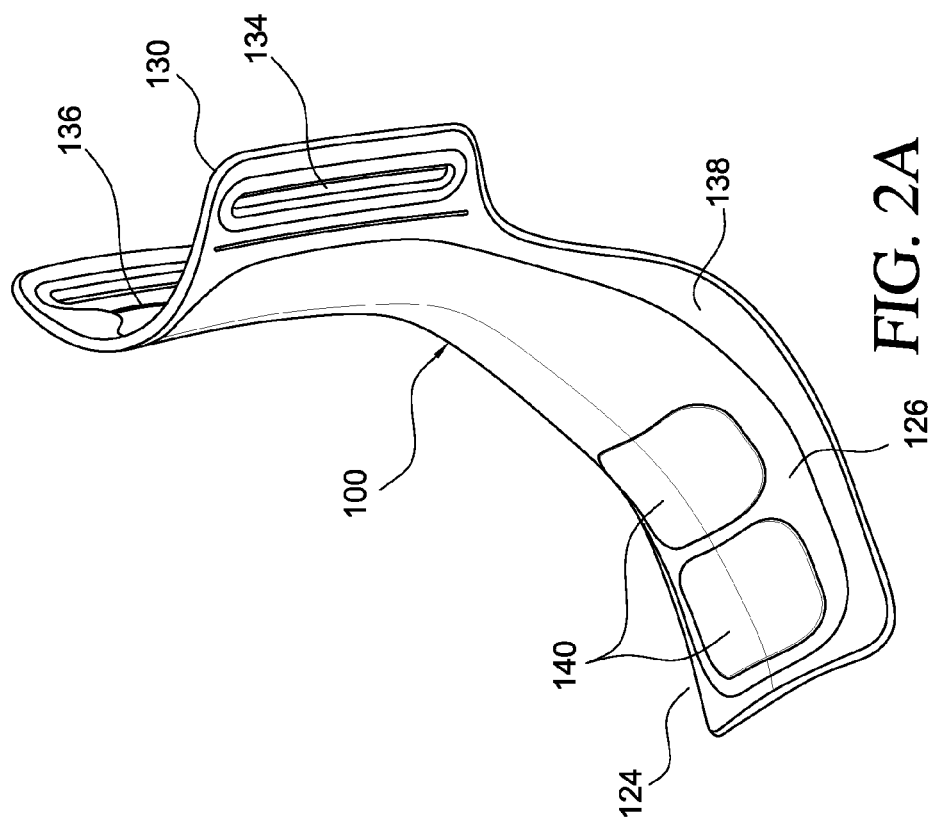
FIG. 2A is a perspective view of a dorsal splint according to an alternate configuration.
Figure 2:
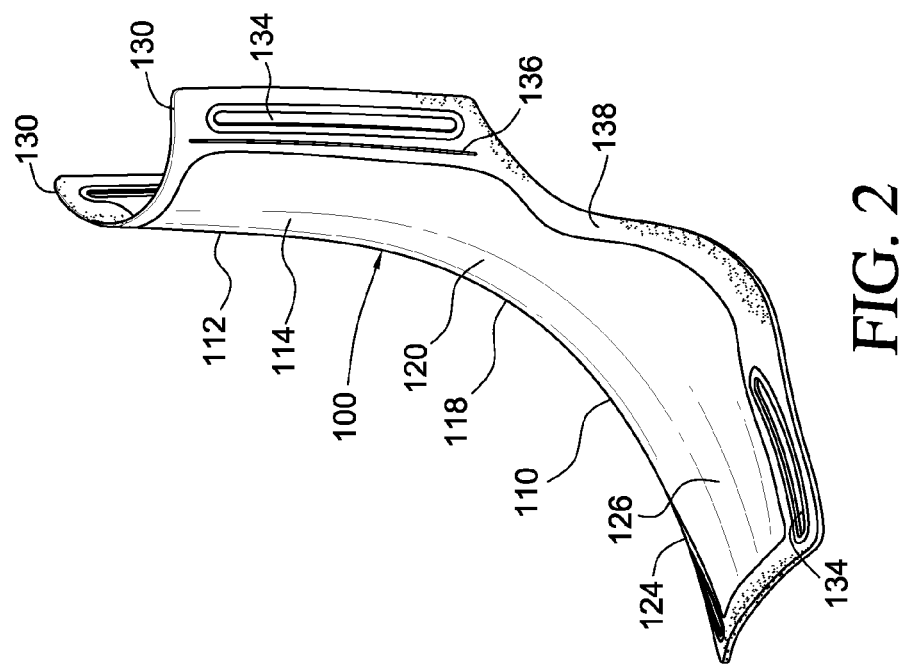
FIG. 2 is a perspective view of a dorsal splint according to another embodiment.

As shown in FIG. 2, if the substantially rigid splint member 110 is utilized without the flexible inner member 142, it may be desirable to provide the overmold 138 extending around the outer edge of the lower portion 124, as well as the upper 112 and intermediate 118 portions. As previously described, the overmold 138 may encompass the slots 134 in the upper 112 and lower 124 portions.

In order to aid with placing the dorsal splint on the user's foot, an elastic band or stockinette may be connected directly to the substantially rigid splint member 110 in any suitable manner, such as by an adhesive. In the case that a stockinette is used, the stockinette may extend along only a portion of the substantially rigid splint member 110, for example, so as to engage only the plantar surface of the foot. Alternatively the stockinette may extend along the entire substantially rigid splint member 110 so as to engage the plantar surface of the foot, the heel, and the calf of a user.

An alternate configuration of a dorsal splint 100 is shown in FIG. 2A. The dorsal splint 100 has the same general configuration as previously discussed. Upper wing portions 130 are delineated from the main dorsal splint 100 via living hinges 136, in the exemplary manner that is discussed above. The wing portions 130 include slots 134 for receiving appropriate strap mechanisms therethrough, in a manner as discussed above. A flexible edge overmold 138 is provided around the entire periphery of the dorsal splint 100.

In order to attach a distal strap thereto, such as any strap disclosed herein, for example in FIGS. 19 and 20A-C, patches 140 of hook material are provided on or embedded in the proximal surface 126 of the lower portion 124 of the dorsal splint 100. Of course, the patches 140 may alternatively be formed of hook receiving material. A skilled artisan will recognize that at least a portion of any suitable strap will have either hook receiving or hook material therein respectively corresponding to the hook or hook receiving material of the patches 140 for selective releasable engagement therewith.

The patches 140 provide an anchor point for any suitable distal strap that is utilized with the dorsal splint 100. Any suitable strap may thus be wrapped around the plantar surface of the foot and the ends thereof may be anchored or engaged with the patches 140. Thus, there is no need for slots in the lower portion 124 of the dorsal splint 100, and the flexible edge overmold 138 may extend around and encompass the entire periphery of the dorsal splint 100.

In alternative embodiments, the substantially rigid splint member 110 may include only the living hinges, and not the overmold, between the wing portions and the upper portion in order to provide the desired amount of flexibility for an improved, closer fit. Alternatively, the substantially rigid splint member 110 may include only the overmold, and not the living hinges, in order to provide a compliant interface between the substantially rigid splint member 110 and the user's skin. Further embodiments are discussed in more detail below.

C. Detailed Description of an Embodiment of a Strap for a Dorsal Splint

As an alternative to utilizing both proximal and distal straps to tighten the dorsal splint 100 to the user's body, a single strap 300 may be utilized, as shown in FIGS. 3A-D.

As shown in FIG. 3A, a substantially rigid splint member 110, having similar features as described above, such as a flexible edge overmold and/or living hinges, is provided. Strap 300 is provided in the shape or form of a "figure 8." More specifically, the strap 300 has first 302 and second 304 ends and first 312 and second 314 surfaces. The first end may be fixed along the distal end of the dorsal splint 100, for example along the lower portion 124 or the intermediate portion 118. Alternatively, the first end 302 may be fixed to the first surface 312 of the strap 300.

The second end 304 is wrapped around the substantially rigid splint member 110 such that the second surface 314 of the strap contacts the proximal surfaces of each of the upper, intermediate, and lower portions, and the first surface 312 of the strap 300 such that the strap crosses over itself along the proximal surface of the intermediate portion and forms first 308 and second loops 310. Loop locks 306 may be provided in order to keep the strap 300 in position with the loops 308, 310 maintained.

In use, the user places the foot through both the loops 308, 310 so the first loop 308 will contract around the plantar surface of the foot and the second loop 310 will contract around the calf of a user. The second end 304 of the strap 300 is pulled to tighten both of the loops 308, 310 simultaneously. The strap 300 may be provided with both hook material and hook receiving material, for example a patch of hook material along the second end 304, such that once the strap 300 has been tightened it may be locked in the tightened position.

Numerous configurations of the "figure 8" strap 300 may be utilized as exemplified in FIGS. 3C and 3D. For example, each loop portion 308, 310 of the strap 300 may include an elastic or stretch portion 316 and a non-stretch portion 318. As shown in FIG. 3D, the elastic or stretch portion 316 and the non-stretch portion 318 may be formed as separate pieces that are attached only along the ends of one or the other of the elastic or stretch portion 316 and the non-stretch portion 318.

The "figure 8" strap may be utilized with any of the disclosed embodiments of a dorsal splint with the appropriate modifications. Specifically, a flexible inner member may be provided between the loops of the strap and the substantially rigid splint member. Or, as described in more detail below, inflatable or non-inflatable air bladders or gel pads may be used between the strap and the plantar surface of the foot.

D. Detailed Description of Another Embodiment of a Dorsal Splint

An embodiment of a dorsal splint 100 is shown in FIGS. 4A-E that is similar to an embodiment discussed above with respect to FIGS. 1A-E, 2, and 2A. The dorsal splint as shown in FIGS. 4A-4E is constructed in a similar manner and from the same materials as discussed above with respect to the embodiments illustrated in FIGS. 1A-E, 2, and 2A.

In a modification from previous embodiments, as exemplified in FIGS. 4A-4E, the overmold 138 encompasses upper wing portions 130, lower wing portions 132, and upper and lower slots 134. Thus, the lower portion 124 provides an enlarged surface area for engaging the dorsal surface of the foot. This configuration provides increased stability and increased support to the dorsal aspect of the foot.

In another variation, while the dorsal splint 100 includes a flexible inner member 142 similar in configuration to those previously discussed, there is no pouch member provided at the distal end of the flexible inner member 142. Instead, the flexible inner member 142 is retained on the substantially rigid splint member 110 via only hook and loop or other appropriate fastening mechanism, as discussed in detail above.

Figure 4A:
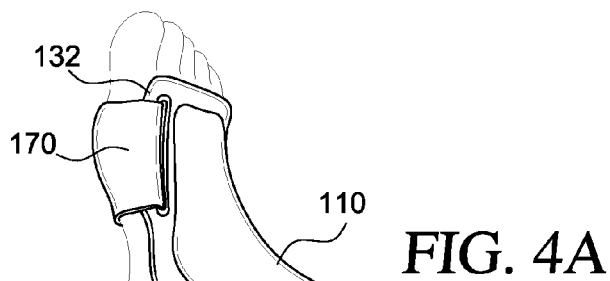
FIGS. 4A-E are various perspective, side, and rear views of another embodiment of a dorsal splint.
Figure 4B:
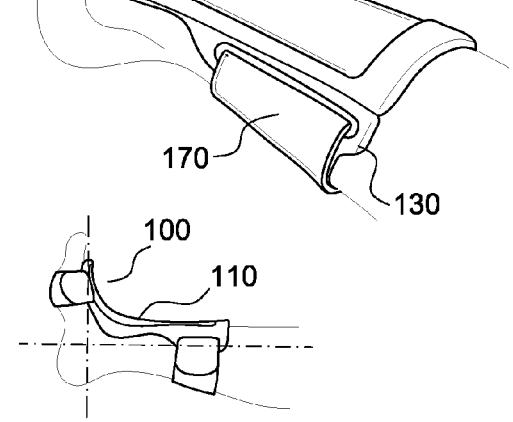
Figure 4C:
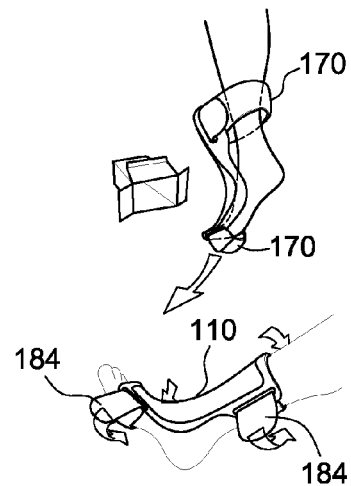
Figure 4D:
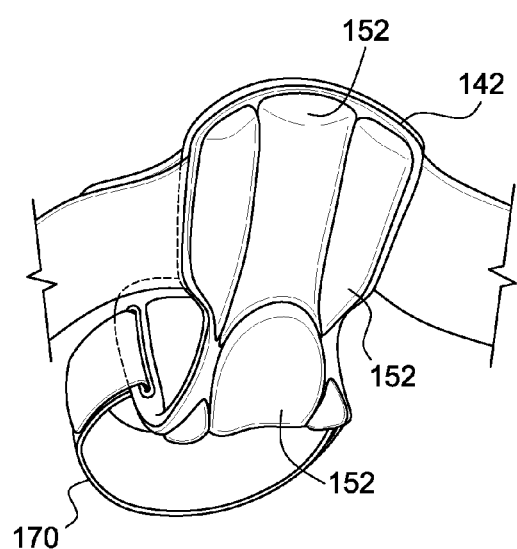
Figure 4E:
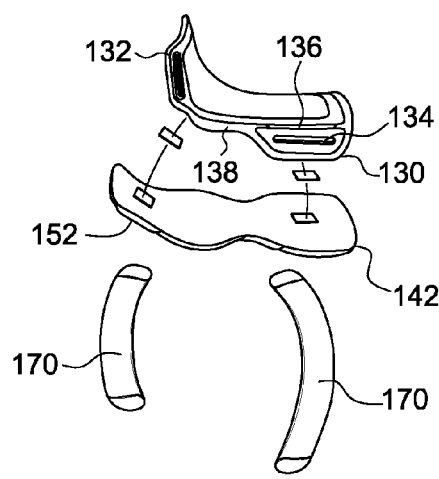

Again, as shown in FIGS. 4A and 4E, "living hinges" 136 are provided in the upper portion 112 between a main a section of the upper portion 112 and the upper wing portions 130 in a manner as described above.

As illustrated in FIG. 4E the flexible inner member 142 has substantially the same shape as the substantially rigid splint member 110. The flexible inner member 142 may be constructed in substantially the same manner as discussed above, without the pouch portion on the proximal surface.

In use, the first surface of the flexible inner member 142 is removably fastened to the posterior and distal surfaces 116, 122, 128 of the upper 112, intermediate 118, and lower 124 portions, as shown in FIG. 4E. Thus the flexible inner member 142 is retained on the substantially rigid splint member 110 so that the dorsal splint 100 may be placed upon the leg, ankle, and foot of the wearer. As an alternative, the flexible inner member 142 may be non-removably connected to the substantially rigid splint member 110 by, for example, an adhesive.

The second surface 146 of the flexible inner member 142 includes or defines at least one padding member 152. A plurality of padding members 152 of varying thickness may be provided in any suitable pattern along the second surface 146, as shown in FIG. 4D. For example, a thicker padded portion may be provided in the area of the intermediate portion in order to protect the bony protuberance of the dorsum. Alternatively, thicker padded portions may also be used to increase the angle of dorsiflexion. The padding may be a thermoform pad having a pattern that provides a "formfit." This may be accomplished by utilizing various thicknesses throughout the pattern. The second surface 146 may be a soft covering that is not receptive to receiving hook material. Of course, any suitable material or fabric will suffice.

Proximal and distal straps 170 are provided for engaging the slots 134 in the upper wing portions 130 and in the lower portion 124. The straps 170 have first 182 and second 184 ends respectively received in the slots 134 and have surfaces carrying or made from hook and/or hook receiving material so that the straps 170 may be fastened onto themselves, as shown in FIGS. 4A-D. Of course, any suitable fastening mechanism, such as snap fasteners or buckles, may be used.

As shown, the straps 170 are positioned between the substantially rigid splint member 110 and the flexible inner member 142, in order to prevent creating points of irritation. The straps may have a uniform or non-uniform shape and size, for example the width may vary along the length of the straps. The straps may be of the same layered construction as previously discussed.

Given the above described construction, and in particular the living hinge, overmold, and padded flexible member, the dorsal splint 100 provides an improved and more comfortable fit for both the user and anyone sharing the bed of the user.

Of course, the dorsal splint 100 may be utilized in numerous variations of the above described embodiment. For example, the substantially rigid splint member 110 may be used without the flexible inner member 142, and may instead have only the proximal and distal straps associated with the slots in the upper and lower portions.

In order to aid with placing the dorsal splint on the user's foot, an elastic band or stockinette may be connected directly to the substantially rigid splint member 110 in any suitable manner, such as by adhesive, or to the flexible inner member 142 in any suitable manner. In the case that a stockinette is used, the stockinette may extend along only a portion of the substantially rigid splint member 110, for example, so as to engage only the plantar surface of the foot. Alternatively the stockinette may extend along the entire substantially rigid splint member 110 so as to engage the plantar surface of the foot, the heel, and the calf of a user.

In alternative embodiments, the substantially rigid splint member 110 may include only the living hinges, and not the overmold, between the wing portions and the upper portion in order to provide the desired amount of flexibility for an improved, closer fit. Alternatively, the substantially rigid splint member 110 may include only the overmold, and not the living hinges, in order to provide a compliant interface between the substantially rigid splint member 110 and the user's skin. Further embodiments are discussed in more detail below.

E. Detailed Description of a Collapsible Embodiment of a Dorsal Splint

A collapsible embodiment of a dorsal splint 500 is shown in FIG. 5.

In this embodiment, a flexible member 510 has a shape that roughly corresponds, and may conform to, the dorsal aspects of a user's lower leg, ankle and foot. The shape includes a generally rectangular shape with a wider portion in the proximal area of the flexible member 510. The flexible member 510 may be formed from any suitable material, and may include a plurality of layers. A suitable layered structure is discussed above with respect to straps 170. Accordingly, the flexible member may include layers of fabric and foam, including layers of hook receiving material.

Amongst and/or within the layers is at least one pouch or pocket 512. In the exemplary, illustrated embodiment, three pouches 512 extend longitudinally along the flexible member 510. Of course, any suitable number of pouches 512 may be used.

Respectively received within the three pouches 512 are three substantially rigid stays or splint members 514. Of course, the number of substantially rigid stays or splint members 514 corresponds to the number of pouches or pockets 512. The substantially rigid splint members 514 may be formed from any suitable material, for example any appropriate thermoplastic or thermosetting polymer, carbon, carbon fiber epoxy composite, plastic, fiber reinforced plastic, molded chopped fibers, laminates, metal or any other suitable material. Exemplary materials include, but are not limited to, nylons, glass filled nylon, polypropylenes, vinyls, polyvinyl chlorides, high density polyethylene, epoxies, urethanes, and polyesters. The substantially rigid splint members 514 may be formed in any suitable manner, for example injection molding, casting, or curing.

The substantially rigid splint members 514 include an upper portion having anterior and posterior surfaces shaped and configured to engage the dorsal aspect of the leg.

An intermediate portion is integrally formed with the upper portion and includes anterior and posterior surfaces and is further shaped and configured to engage the dorsum. As an alternative, the intermediate portion may be formed as a separate piece from the upper portion. The distinct pieces may be connected to each other in any suitable manner, such as by welding or adhesives.

A lower portion is integrally formed with the intermediate portion in order to form the substantially rigid splint members. Proximal and distal surfaces are provided on the lower portion. As an alternative, the lower portion may be formed as a separate piece from the intermediate portion. The distinct pieces may be connected to each other in any known suitable manner, such as by welding or adhesives.

Thus, the substantially rigid splint members 514 comprise three portions, an upper portion, an intermediate portion, and a lower portion. Each portion is shaped and configured to engage a respective portion of the wearer's body. For example, the upper posterior surface may be generally flat or concave in shape in order to accommodate the fore leg, or shin. The shape of a concavity may be uniform or non-uniform along the posterior surface.

In order to provide a low profile dorsal splint, the upper anterior surface may have a flat or contoured shape to match the shape of the upper posterior surface. The upper portion may have any suitable thickness in order to provide the appropriate rigidity and support to the dorsal splint. The thickness may be uniform or non-uniform across the width, and along the length of the upper portion.

The intermediate portion is shaped and configured to engage the dorsal aspect of the user's ankle Accordingly, like the upper portion, the posterior surface of the intermediate portion may have a substantially flat or concave shape to accommodate the user's ankle Similarly to the upper portion, the shape of a concavity may be uniform or non-uniform. The thickness of the intermediate portion may also be uniform or non-uniform. The proximal end of the intermediate portion is merged with the distal end up the upper portion and provides a smooth transition such that a point of irritation is not created at the juncture. Of course, if the intermediate and upper portions are separately formed and joined together, any appropriate surface treatment, such as sanding, grinding, or polishing, may be utilized to provide a smooth transition.

Similarly, the lower portion is shaped and configured to engage the dorsal aspect of the user's foot. Thus, the distal surface of the lower portion may have a substantially flat or concave shape. As with the upper and intermediate portions, a concavity and thickness of the lower portion may be uniform or non-uniform. In a similar fashion as discussed above, the proximal end of the lower portion is merged with the distal end of the intermediate portion in order to provide a smooth transition between the two portions.

The combination of the three portions serves to position a user's foot, ankle, and lower leg in a dorsiflexion position when used in combination with the flexible member 510. The angle of dorsiflexion may be fixed by the relationship of the three members. Exemplary angles of dorsiflexion are in the range of 80° to 90°. In particular, a range of 85° to 90° provides a suitable range of dorsiflexion.

In use, the substantially rigid splint members 514 are received in the pockets or pouches 512 of the flexible member 510. The pouches or pockets 512 may have openings at either end, or along the length of the pouches, in order to receive the substantially rigid splint members 514. The openings may always be open, in order to allow the substantially rigid splint members 514 to be removably received therein. Or the openings may be closed, in a known manner, once the substantially rigid splint members 514 have been received therein. For example, the openings may be sewn shut. Alternatively, zipper, snap, or hook and loop closures may be provided to allow selective closure of the openings in order to allow selective removal of the substantially rigid splint members 514 from the pockets or pouches 512. Thus, the brace is collapsible in order to fit into a smaller package.

The pouches or pockets 512 and the substantially rigid splint members 514 are slightly spaced from each other in order to allow the flexible member to more easily conform to the curved surfaces of the dorsal aspects of the user's lower leg, ankle, and foot, and to collapse into a flat configuration when not in use. Additionally, the wider portion of the proximal end of the flexible member 510 may have no rigid splints or stays in order to provide a more comfortable fit.

Straps of any suitable configuration, as discussed herein, are provided. For example, the flexible member 510 may be formed of softgood, and straps may be sewn to the flexible member 510 at one end. The straps may carry hook material at the other end in order to be fixed directly to the flexible member 510 or to the straps themselves. Alternatively, the flexible member 510 may include slotted loops for receiving ends of straps, in a manner previously discussed.

Further embodiments of a dorsal splint are discussed in more detail below.

F. Detailed Description of an Embodiment of a Hybrid Dorsal Splint

An embodiment of a hybrid dorsal splint 600 is shown in FIGS. 6A and 6B.

A substantially rigid splint member 602 may be constructed in a similar manner and with similar materials as previously discussed with respect to various other embodiments. As described with respect to previous embodiments, the substantially rigid splint member 602 includes upper, intermediate, and lower portions having anterior and posterior/distal surfaces shaped and configured to engage the dorsal aspects of the leg.

Thus, the substantially rigid splint member 602 comprises three portions, an upper portion, an intermediate portion, and a lower portion. Each portion is shaped and configured to engage a respective portion of the wearer's body. For example, the upper posterior surface may be generally flat or concave in shape to accommodate the leg, or shin.

The intermediate portion is shaped and configured to engage the dorsal aspect of the user's ankle Accordingly, like the upper portion, the posterior surface of the intermediate portion may have a substantially flat or concave shape to accommodate the user's ankle Similarly, the lower portion is shaped and configured to engage the dorsal aspect of the user's foot. Thus, the distal surface of the lower portion may have a substantially flat or concave shape.

Thus, the combination of the three portions serves to position a user's foot, ankle, and lower leg in a dorsiflexion position. The angle of dorsiflexion may be fixed by the relationship of the three members. Exemplary angles of dorsiflexion are in the range of 80° to 90°. In particular, a range of 85° to 90° provides a suitable range of dorsiflexion.

The "hybrid" aspect of this embodiment of a dorsal splint arises from the addition of flexible members 604, 608 to the substantially rigid splint member 602 as an alternative to the flexible edge overmold of previous embodiments. The flexible members 604, 608 may be fixed to the substantially rigid splint member 602 to provide a comfortable and close fit between the dorsal splint 600 and the user's leg. A flexible inner member 614 may also be provided, similar to those previously discussed.

The flexible members 604, 608 may be positioned as upper and intermediate or lower flexible members. The upper and intermediate or lower flexible members 604, 608 may attached to the substantially rigid splint member 602 in any suitable manner, either in a fixed or removable manner. For example, fasteners, such as rivets, 612 are provided. Since these elements are riveted strategically on and along the curvature of the main shell of the substantially rigid splint member 602, the overall dorsal splint maintains rigidity when it is worn, even with the use of thin flexible members 604, 608. Of course, any suitable fastening system, such as adhesive or snap fasteners, may also be used.

The upper and intermediate or lower flexible members 604, 608 have a width greater than the substantially rigid splint member 602 in order to define flexible wing portions 606, 610. The flexible wing portions 606, 610 allow the dorsal splint 600 to better conform to the user's body, in order to provide a closer and more comfortable fit. The flexible members 604, 608 also flex inwardly in order to fit into a smaller package.

The flexible members 604, 608 may be formed from any suitable material, for example a thermoset polymer, such as solid polyurethane. Of course any suitable material, such as a thermoplastic elastomer, may be used.

As previously mentioned, in order to provide an even more comfortable and closer fit, a flexible inner member 614, such as any of those previously discussed, is also provided. Further, any suitable strapping mechanism, such as those discussed above and below, may be provided in order to retain the dorsal splint 600 in position on the user's body.

Further embodiments of a dorsal splint are discussed in more detail below.

G. Detailed Description of an Embodiment of an Integral Dorsal Splint

Figure 7:
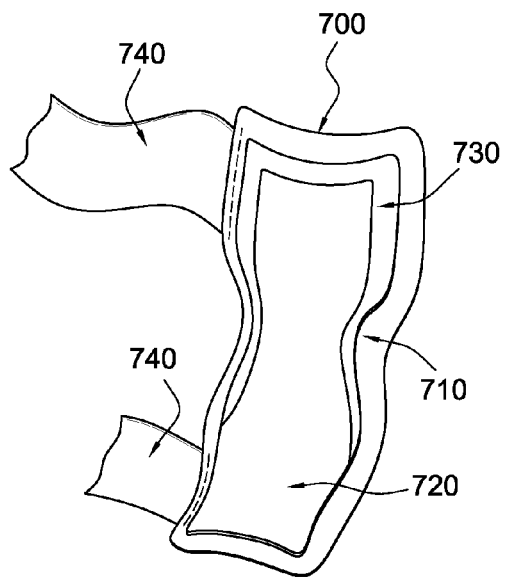
FIG. 7 is a front perspective view of another embodiment of a dorsal night splint.

An embodiment of an integral dorsal splint 700 is shown in FIG. 7. The integral dorsal splint 700 includes a flexible member 710 and defines surfaces which act as an interface between the dorsal splint 700 and the dorsal aspects of the leg. A substantially rigid splint member 720 having a flexible edge overmold 730 is integrally formed on the proximal surfaces of the flexible member 710.

The substantially rigid splint member 720 may have a similar configuration as previously discussed. The flexible edge overmold 730 encases an outer edge of at least the upper portion, and as shown encases an outer edge of both the upper portion and the intermediate portion. Of course, the overmold 730 may encase the outer edge of the lower portion as well.

Both the substantially rigid splint member 720 and the overmold 730 may be formed by injection molding directly onto and integrally with the flexible member 710.

In order to provide an even closer and more comfortable fit, the dorsal splint 700 utilizes the flexible member 710 to provide a compliant surface interface between the dorsal splint 700 and the dorsal aspects of the leg. The flexible member 710 may be softgood, or a sheet of material, such as a polypropylene knit material, a polyester knit material, a nylon, or any other suitable slightly porous material to allow the materials of the rigid splint member 720 and the overmold 730 to pass therethrough to be become integrated with the flexible member 710.

As shown in FIG. 7, the substantially rigid splint member 720 and the overmold 730 are integrally formed with the flexible member 710 by injection molding. The pores of the flexible member 710 allow the plastic or polymer material of the substantially rigid splint member 720 and the overmold 730 to pass through the flexible member 710 and to bind the flexible member 710 to the substantially rigid splint member 720 and the overmold 730.

Thus the flexible member 710 provides a soft and compliant interface between the surfaces of the substantially rigid splint member 720 and the body of the user. This allows the dorsal splint 700 to more closely conform to the user's body.

Proximal and distal straps 740 are provided to maintain the dorsal splint 700 on the body of the user. The straps 740 may be sewn or otherwise attached to the flexible member 710, for example via slots and loops along the edges of the flexible member 710. Alternatively, straps 740 may be riveted or otherwise fastened to the anterior and proximal surfaces of the substantially rigid splint member 720. Straps 740 may be of any suitable type or construction, such as those discussed above and below.

The overmold 730 and flexible member 710 provide a flexible interface between the rigid edges of the substantially rigid splint member 720 and the user's body. Thus, irritation due to the hard and sometimes sharp edges is reduced or eliminated. Accordingly, the dorsal splint 700 provides a more comfortable fit for the prolonged use during sleeping for both the user and any person sharing the same bed as the user. These features are an improvement over conventional dorsal splints that do not provide adequate protection from the rigid, and sometimes sharp, edges of the dorsal splints.

In alternative embodiments, living hinges, of the type described herein, may be provided to increase the flexibility of the wider portions of the dorsal splint 700 in order to allow greater conformance to the user's body. Further embodiments of a dorsal splint are discussed in more detail below.

H. Detailed Description of an Embodiment of an Alterable Dorsal Splint

Figure 8A:
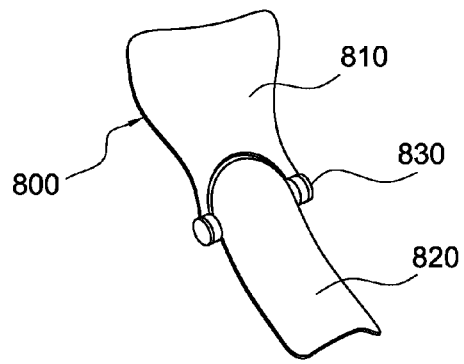
FIGS. 8A-C are various front perspective views of another embodiment of a dorsal night splint.
Figure 8B:
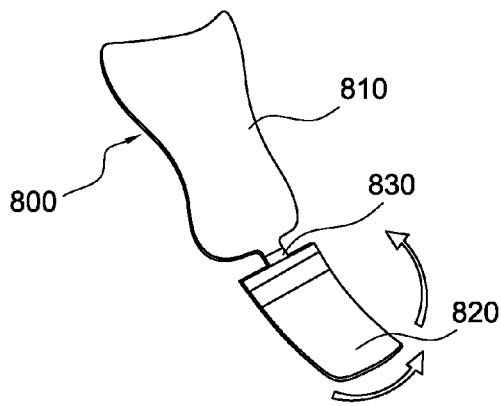
Figure 8C:
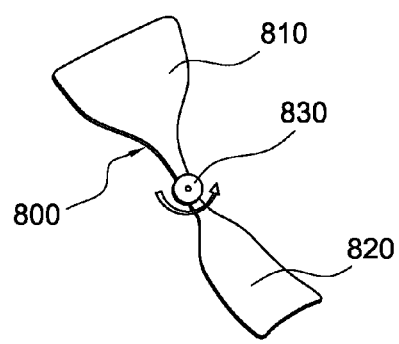

An embodiment of an alterable dorsal splint 800 is shown in FIGS. 8A-C.

The alterable dorsal splint 800 includes substantially rigid upper and lower splint members 810, 820.

The upper member 810 includes anterior and posterior surfaces and is shaped and configured to engage the dorsal aspect of the lower leg. The upper member further includes first and second wing portions extending respectively from first and second sides of the upper portion. The upper posterior surface is generally concave in shape to accommodate the fore leg, or shin. The shape of the concavity may be uniform or non-uniform along the posterior surface. In order to provide a low profile dorsal splint, the upper anterior surface may have a contoured shape to match the shape of the upper posterior surface. The upper portion may have any suitable thickness in order to provide the appropriate rigidity and support to the dorsal splint 800. The thickness may be uniform or non-uniform across the width, and along the length of the upper portion.

The lower portion 820 is shaped and configured to engage the dorsal aspect of the user's foot. Thus, the distal surface of the lower portion has a substantially concave shape. A flared distal end portion may be provided to avoid rigid corners that would dig into the flesh of the dorsal surface of the user's foot. As with the upper portion, the concavity and thickness of the lower portion may be uniform or non-uniform.

An intermediate connector portion 830, such as a hinge or joint, is provided between the upper 810 and lower 820 portions. The intermediate connector portion 830 is formed to allow relative rotation between the upper 810 and lower 820 portions in order to reduce the overall size or length of the dorsal splint 800 when the splint is not in use.

A flexible edge overmold or living hinges, as previously discussed, may be provided for one or both of the upper 810 and lower 820 portions. A suitable flexible inner member and/or suitable fastening and tightening mechanisms, as discussed above and below, may also be provided.

As shown in FIG. 8A, a flip type hinge is provided as the intermediate connector portion 830. This hinge type is common in mobile phones, and may be referred to as a "flip phone" hinge. This hinge allows the upper 810 and lower 820 portions to be opened and closed in a manner so that when closed, the lower portion 820 lies against the upper portion 810. In this manner the overall length of the dorsal splint 800 is reduced when the splint is not in use.

The hinge may be provided with suitable locking mechanisms, as will be recognized by the skilled artisan, such as a spring biasing mechanism, in order to prevent the accidental movement of the upper 810 and lower 820 portions with respect to each other.

In an alternate configuration, as shown in FIG. 8B, a ball joint swivel bearing connection is provided. This connection provides relative rotation between the upper 810 and lower 820 portions in three axes. A locking mechanism may be provided to lock the upper 810 and lower 820 portions from relative movement, as will be recognized by a skilled artisan. In this manner the angle of dorsiflexion may be adjusted. Also the dorsal splint 800 may be adjusted for different inherent angles of abduction/adduction in user's feet. Of course, when the dorsal splint is not in use the upper 810 and lower 820 portions may be rotated to lie against each other in order to reduce the overall size and length of the splint.

In yet another alternate configuration, as shown in FIG. 8C, a single axis swivel connection is provided such that the upper 810 and lower 820 portions may be rotated in substantially a plane to lie against one another. As previously discussed, this allows the overall size and length of the dorsal splint 800 to be reduced.

The combination of the three portions serves to position a user's foot, ankle, and lower leg in a dorsiflexion position. The angle of dorsiflexion may be fixed or altered by the relationship of the three members. Exemplary angles of dorsiflexion are in the range of 80° to 90°. In particular, a range of 85° to 90° provides a suitable range of dorsiflexion.

Further embodiments of a dorsal splint are discussed in more detail below.

I. Detailed Description of an Embodiment of a Strap for a Dorsal Splint

Figure 9:
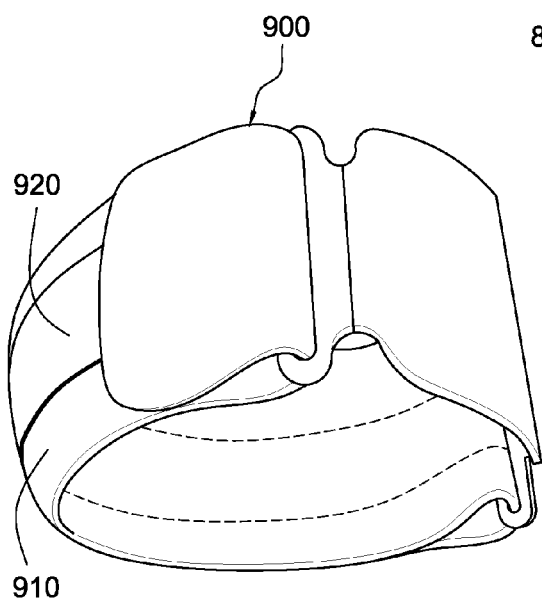
FIG. 9 is a bottom perspective view of an embodiment of a strap for use with various embodiments of a dorsal splint.

An embodiment of a flexible (or flex) edge strap 900 for use with a dorsal splint is shown in FIG. 9.

The flex edge strap 900 is formed from two layered materials. The first layer of material 910 may be a thin layer of flexible material such as urethane foam or neoprene. The first layer of material 910 has or defines a first width.

The second layer of material 920 may be layer of non-stretch material, such as woven nylon. The second layer 920 further includes hook receiving material. The second layer 920 has a width that is less than the width of the first layer 910 of flexible material.

The two layers 910, 920 are connected together in any suitable manner, such as by sewing or adhesive. The second layer 920 may be centered along the first layer 910, or may be offset or aligned along an edge of the first layer 910. The second layer 920 may be provided along the entire length of the first layer 910, or only along selected portions of the first layer 910. In this manner the lengthwise stretch of the strap may be controlled by the second, non-stretch layer 920.

When the second layer 920 is centered along the length of the first layer 910 the strap 900 becomes a flexible edge strap. The strap 900 is therefore able to conform to the anatomy of the user so as to reduce pressure points. The width of the second, non-stretch layer 920 may be varied to alter the amount of flex along the edges of the strap 900.

Hook material is provided along the ends of the strap 900 so that the strap 900 may be closed against itself when the hook material engages with the hook receiving material of the second, non-stretch layer 920.

A skilled artisan will recognize many suitable materials that may be used to form each of the layers of the strap 900. The strap 900 may be utilized in any of the above or below discussed embodiments of a dorsal splint.

Further embodiments of a dorsal splint are discussed in more detail below.

J. Detailed Description of another Embodiment of a Collapsible Dorsal Splint

Another embodiment of a collapsible dorsal splint 1000 is shown in FIGS. 10A and 10B.

In the embodiment shown in FIGS. 10A and 10B, a flexible member 1030, includes first, second, third, and fourth pockets 1032, 1034, 1036, 1038. The first and second pockets 1032, 1034 extend lengthwise along either the first and second sides of the flexible member 1030 from the proximal end towards the distal end, and are formed along a centerline of the flexible member 1030. The pockets 1032, 1034 extend to the point in the flexible member 1030 of the transition between the ankle engaging portion and the foot engaging portion. Alternatively, the pockets 1032, 1034 may extend the entire length of the flexible member 1030. Of course, more than two pockets may be utilized.

The flexible member 1030 having a shape and configuration to conform to the dorsal surfaces of the lower leg, ankle, and foot is provided. The flexible member 1030 may be made from any suitable materials, such as softgood, foam covered with suitable fabrics, or any other suitable materials. The flexible member 1030 is provided with at least one pocket or pouch along a first or second surface.

The pockets 1032, 1034 may be formed in any suitable manner, such as by layers of fabric connected along the edges of one of the layers by threads, adhesive, or in any other suitable manner. The pockets may each have an open end along the proximal end of the flexible member 1030. Alternatively, the openings may be along the distal end, or along either surface of the flexible member 1030. The open ends may be maintained open or closed off in a manner described below.

Substantially rigid first and second splint members 1010, 1020 are provided to be received within the first and second pockets 1032, 1034. The splint members 1010, 1020 may have upper, intermediate, and lower portions that are shaped and configured to engage the dorsal aspect of the lower leg, ankle, and at least a portion of the foot. Alternatively, the splint members 1010, 1020 may have upper, intermediate, and lower portions that are shaped and configured to engage the dorsal aspect of the lower leg, ankle, and a substantial portion of the foot.

The substantially rigid splint members 1010, 1020 may be formed from any suitable material, for example any appropriate thermoplastic or thermosetting polymer, carbon, carbon fiber epoxy composite, plastic, fiber reinforced plastic, molded chopped fibers, laminates, metal or any other suitable material. Exemplary materials include, but are not limited to, nylons, glass filled nylon, polypropylenes, vinyls, polyvinyl chlorides, high density polyethylene, epoxies, urethanes, and polyesters. The substantially rigid splint members 1010, 1020 may be formed in any suitable manner, for example injection molding, casting, or curing.

Each substantially rigid splint member 1010, 1020 includes anterior and posterior surfaces that may have the desired amount of uniform or non-uniform curvature in order to be complementary shaped to the user's lower leg, ankle and foot. A skilled artisan will recognize that the splint members 1010, 1020 may have any suitable and desired shape. For example, the splint members 1010, 1020 may be wider at a proximal end and narrower at the distal end. The width may vary in a uniform or non-uniform manner in order to provide a comfortable fit for the user.

The first and second splint members 1010, 1020 are either removably or fixedly received in the first and second pockets 1032, 1034. The splint members 1010, 1020 are slid into the pockets. If it is desired to maintain the splint members 1010, 1020 fixedly in the pockets 1032, 1034, the open ends may be closed or selectively closed by threads, adhesives, zipper closures, or any other suitable manner.

The flexible member 1030 also includes third and fourth pockets 1036, 1038, which may be formed as discussed above. The third and fourth pockets 1036, 1038 extend from the distal end towards the proximal end of the flexible member 1030. The third and fourth pockets 1036, 1038 are shaped to extend along the first and second sides of the flexible member 1030 and along the distal portions of the first and second pockets 1032, 1034. The pockets 1036, 1038 include open ends at the distal ends. Alternatively, the open ends may be provided at the proximal ends or along either surface of the flexible member 1030. They may be provided with any suitable shape.

First and second substantially rigid removable stays (or splint members) 1040, 1050, are provided for insertion into the third and fourth pockets 1036, 1038. While the stays 1040, 1050 are described as removable, they may also be fixed within the pockets as discussed above with respect to the splint members 1010, 1020. The stays 1040, 1050 may be formed in the same manner as the splint members 1010, 1020, and from any of the materials listed above. The stays 1040, 1050 may be shaped and configured to engage the dorsal aspect of the user's foot, and at least a portion of the dorsal aspect of the ankle Straps 1060 of any suitable configuration are provided at least along the proximal and distal portions of the dorsal splint 1000. The straps 1060 may include hook material and/or hook receiving material, or any other suitable fasteners, such as buckles or snap fasteners.

The substantially rigid portions combined serve to position a user's foot, ankle, and lower leg in a dorsiflexion position. The angle of dorsiflexion may be fixed by the relationship of the three members. Exemplary angles of dorsiflexion are in the range of 80° to 90°. In particular, a range of 85° to 90° provides a suitable range of dorsiflexion.

The use of two splint members 1010, 1020 and stays (or splint members) 1040, 1050 to essentially divide the dorsal splint 1000 in half, allows the dorsal splint 1000 to take a lower profile while not attached to a user, for ease of storage. This configuration further allows the dorsal splint 1000 to better conform to the user's lower leg, ankle, and foot, by allowing the splint 1000 to flex around its centerline. Of course, if the splint members 1010, 1020 and stays 1040, 1050 are allowed to be removable, the flexible member may be completely flattened and collapsed, thus reducing the space required for storage. Thus, the dorsal splint 1000 is more suitable for travel, so a user may use the splint every night, even while traveling.

K. Detailed Description of Another Embodiment of a Collapsible Dorsal Splint

Another embodiment of a collapsible dorsal splint 1100 is shown in FIG. 11.

The flexible member 1130 is provided with at least one pocket or pouch along a first or second surface.

As shown in FIG. 11, a flexible member 1130 includes a single pocket or pouch 1132 that extends length-wise along the entire flexible member 1130. The pocket may be open at a proximal end, or along the distal end, or along either surface of the flexible member 1130. First, second, and third splint members 1110, 1120, 1122 are either removably or fixedly received in pockets 1132. The splint members 1110, 1120, 1122 are slid into the pockets. If it is desired to maintain the splint members 1110, 1120, 1122 fixedly in the pocket 1032 the open ends may be closed or selectively closed by threads, adhesives, zipper closures, or in any other suitable manner.

Substantially rigid first and second splint members 1110, 1120 are provided to be received within the pockets 1032. The splint members 1110, 1120 have upper, intermediate, and lower portions that are shaped and configured to engage the dorsal aspect of the lower leg, ankle, and at least a portion of the foot. Alternatively, the splint members 1110, 1120 may have upper, intermediate, and lower portions that are shaped and configured to engage the dorsal aspect of the lower leg, ankle, and a substantial portion of the foot.

A third splint member 1122 is provided between the first and second splint members 1110, 1120. The third splint member 1122 may be rigid in the manner of the other splint members, or alternatively, may be made from a flexible material, such as plastic. Suitable materials may include thermoplastic elastomers, silicones, or urethanes.

The flexible member 1130 may be similar to the previously discussed flexible member. The flexible member 1130 has a shape and configuration to conform to the dorsal surfaces of the lower leg, ankle, and foot. The flexible member 1130 may be made from any suitable materials, such as softgood, foam covered with suitable fabrics, or any other suitable materials.

The substantially rigid splint members 1110, 1120 may be formed from any suitable material, for example any appropriate thermoplastic or thermosetting polymer, carbon, carbon fiber epoxy composite, plastic, fiber reinforced plastic, molded chopped fibers, laminates, metal or any other suitable material. Exemplary materials include, but are not limited to, nylons, glass filled nylon, polypropylenes, vinyls, polyvinyl chlorides, high density polyethylene, epoxies, urethanes, and polyesters. The substantially rigid splint members 1110, 1120 may be formed in any suitable manner, for example injection molding, casting, or curing.

Each substantially rigid splint member 1110, 1120 includes anterior and posterior surfaces that have the desired amount of uniform or non-uniform curvature in order to be complementary shaped to the user's lower leg, ankle and foot. A skilled artisan will recognize that the splint members 1110, 1120 may have any suitable and desired size and shape. For example, the splint member 1110, 1120 may be wider at a proximal end and narrower at the distal end. The width may vary in a uniform or non-uniform manner in order to provide a comfortable fit for the user. Further, the thickness may also vary in any suitable manner.

Straps 1140 of any suitable configuration are provided at least at the proximal and distal portions of the dorsal splint 1000. The straps 1140 may include hook material and/or hook receiving material, or any other suitable fasteners, such as buckles or snap fasteners.

The substantially rigid portions combined serve to position a user's foot, ankle, and lower leg in a dorsiflexion position. The angle of dorsiflexion may be fixed by the relationship of the three members. Exemplary angles of dorsiflexion are in the range of 80° to 90°. In particular, a range of 85° to 90° provides a suitable range of dorsiflexion.

The use of two splint members 1110, 1120 connected by a third, flexible, splint member 1122 to essentially divide the dorsal splint 1100 in half, allows the dorsal splint 1100 to take a lower profile while not attached to a user, for ease of storage and for reduced shelf space during display. This configuration further allows the dorsal splint 1100 to better conform to the user's lower leg, ankle, and foot, by allowing the splint 1100 to flex around its centerline.

Of course, if the splint members 1110, 1120, 1122 are allowed to be removable, the flexible member may be completely flattened and collapsed, thus reducing the space required for storage. Thus, the dorsal splint 1100 is more suitable for travel, so a user may use the splint every night, even while traveling. Additionally, the dorsal splint 1100 may be collapsed and packaged for sale in a smaller container, and thus may save sale display and shelf space, such that more dorsal splints 1100 may be displayed in a defined amount of space.

L. Detailed Description of Another Embodiment of a Collapsible Dorsal Splint

Another embodiment of a collapsible dorsal splint 1200 is shown in FIG. 12.

A flexible member 1230, similar to the previously discussed flexible member, has a shape and configuration to conform to the dorsal surfaces of the lower leg, ankle, and foot is provided. The flexible member 1230 may be made from any suitable materials, such as softgood, foam covered with suitable fabrics, or any other suitable materials. The flexible member 1230 may be provided with at least one pocket or pouch along a first or second surface.

As shown in FIG. 12, the flexible member 1230 includes a plurality of pockets or pouches 1240 that apportion the width and length along the entire flexible member 1230. The pockets may be open at proximal ends, along distal ends, or along either surface of the flexible member 1230.

Substantially rigid segmented splint members 1220 are provided to be received within the pockets 1240. The splint members 1220 have portions that are shaped and configured to engage portions of the dorsal aspect of the lower leg, ankle, and the foot.

The substantially rigid segmented splint members 1220 may be formed from any suitable material, for example any appropriate thermoplastic or thermosetting polymer, carbon, carbon fiber epoxy composite, plastic, fiber reinforced plastic, molded chopped fibers, laminates, metal or any other suitable material. Exemplary materials include, but are not limited to, nylons, glass filled nylon, polypropylenes, vinyls, polyvinyl chlorides, high density polyethylene, epoxies, urethanes, and polyesters. The substantially rigid splint members 1220 may be formed in any suitable manner, for example injection molding, casting, or curing.

Each substantially rigid splint member 1220 includes anterior and posterior surfaces that have the desired amount of uniform or non-uniform curvature in order to be complementary shaped to the appropriate portion of the user's lower leg, ankle and foot. A skilled artisan will recognize that the splint members 1220 may have any suitable and desired shape.

The splint members 1220 are either removably, or fixedly, received in pockets 1240. The splint members 1220 are inserted into the pockets. If it is desired to maintain the splint members 1220 fixedly in the pocket 1240 the open ends may be closed or selectively closed by threads, adhesives, zipper closures, or any other suitable manner.

Straps of any suitable configuration are provided at least at the proximal and distal portions of the dorsal splint 1200. The straps may include hook material and/or hook receiving material, or any other suitable fasteners, such as buckles or snap fasteners.

The substantially rigid portions combined serve to position a user's foot, ankle, and lower leg in a dorsiflexion position. The angle of dorsiflexion may be fixed by the relationship of the three members. Exemplary angles of dorsiflexion are in the range of 80° to 90°. In particular, a range of 85° to 90° provides a suitable range of dorsiflexion.

The use of a plurality of splint members 1240, allows the dorsal splint 1200 to take a collapsed lower profile while not attached to a user, for ease of storage. This configuration further allows the dorsal splint 1200 to better conform to the user's lower leg, ankle, and foot, by allowing the splint 1200 to flex around the user's lower leg, ankle, and foot. Of course, if the splint members 1240 are allowed to be removable, or are appropriately shaped, the flexible member may be completely flattened or nearly completely flattened, thus reducing the space required for storage. Thus, the dorsal splint 1200 is more suitable for travel, so a user may use the splint every night, even while traveling.

M. Detailed Description of Another Embodiment of a Collapsible Dorsal Splint

Another embodiment of a collapsible dorsal splint 1300 is shown in FIGS. 13A-C.

A flexible member 1330, similar to the previously discussed flexible member, has a shape and configuration to conform to the dorsal surfaces of the lower leg, ankle, and foot is provided. The flexible member 1330 may be made from any suitable materials, such as softgood, foam covered with suitable fabrics, or any other suitable materials. The flexible member 1330 is provided with at least one pocket or pouch along a first or second surface.

As shown in FIG. 13B, the flexible member 1330 includes a single pocket or pouch 1332 that extends length-wise along the flexible member 1330. The pocket may be open at a proximal end, or along the distal end, or along either surface of the flexible member 1330.

Substantially rigid first and second splint members 1310, 1320 are provided to be received within the pockets 1032. The splint members 1310, 1320 have upper, intermediate, and lower portions that are shaped and configured to engage the dorsal aspect of the lower leg, ankle, and at least a portion of the foot. Alternatively, the splint members 1310, 1320 may have upper, intermediate, and lower portions that are shaped and configured to engage the dorsal aspect of the lower leg, ankle, and a substantial portion of the foot.

The substantially rigid splint members 1310, 1320 may be formed from any suitable material, for example any appropriate thermoplastic or thermosetting polymer, carbon, carbon fiber epoxy composite, plastic, fiber reinforced plastic, molded chopped fibers, laminates, metal or any other suitable material. Exemplary materials include, but are not limited to, nylons, glass filled nylon, polypropylenes, vinyls, polyvinyl chlorides, high density polyethylene, epoxies, urethanes, and polyesters. The substantially rigid splint members 1310, 1320 may be formed in any suitable manner, for example injection molding, casting, or curing.

Each substantially rigid splint member 1310, 1320 includes anterior and posterior surfaces that have the desired amount of uniform or non-uniform curvature in order to be complementary shaped to the user's lower leg, ankle and foot. A skilled artisan will recognize that the splint members 1310, 1320 may have any suitable and desired shape. For example, the splint members 1310, 1320 may be wider at a proximal end and narrower at the distal end. The width may vary in a uniform or non-uniform manner in order to provide a comfortable fit for the user.

The first and second splint members 1310, 1320 are either removably, or fixedly, received in the pocket 1332. The splint members 1310, 1320 may be temporarily connected to each other along their length and then may be slid into the pocket 1332. If it is desired to maintain the splint members 1310, 1320 fixedly in the pocket 1332 the open end may be closed or selectively closed by threads, adhesives, zipper closures, or any other suitable manner.

Straps 1340 of any suitable configuration are provided at least at the proximal and distal portions of the dorsal splint 1300. The straps 1340 may include hook material and/or hook receiving material, or any other suitable fasteners, such as buckles or snap fasteners.

The substantially rigid portions combined serve to position a user's foot, ankle, and lower leg in a dorsiflexion position. The angle of dorsiflexion may be fixed by the relationship of the three members. Exemplary angles of dorsiflexion are in the range of 80° to 90°. In particular, a range of 85° to 90° provides a suitable range of dorsiflexion.

The use of two splint members 1310, 1320 to essentially divide the dorsal splint 1300 in half, allows the dorsal splint 1300 to take a collapsed or lower profile while not attached to a user, for ease of storage. This configuration further allows the dorsal splint 1300 to better conform to the user's lower leg, ankle, and foot, by allowing the splint 1300 to flex around its centerline. Of course, if the splint members 1310, 1320 are allowed to be removable, the flexible member may be completely collapsed or flattened, thus reducing the space required for storage. Thus, the dorsal splint 1300 is more suitable for travel, so a user may use the splint every night, even while traveling.

In an alternative embodiment, first, second, and third substantially rigid splint members may be provided and three pockets may be provided within the flexible member. The first and second splint members may be sewn in, or otherwise fixedly received within first and second pockets in the flexible member. The third splint member may then be removable received within the third pocket, in a manner previously discussed. Thus, the dorsal splint may have a lower profile when not in use to reduce the amount of storage space required.

N. Detailed Description of Various Embodiments of a Dorsal Splint

Various embodiments of a dorsal splint 100 are illustrated in FIGS. 14, 15, 16, and 17A-C. The dorsal splint 100 of these embodiments has the same basic structure and configuration as discussed above with respect to the embodiments shown in FIGS. 1A-E, 2, 2A, and 4A-E.

As shown in FIG. 14, instead of a strap of hook and hook receiving material, an elastic fabric strap 170 is provided. The strap may have any suitable configuration to provide a comfort fit, such as an elongated opening along the portion of the strap that contacts the plantar surface of the foot.

As shown in FIG. 15, a pad or bladder 196 is provided between the strap 170 and the plantar surface of the foot. Any suitable pad 196 may be used, such as a gel pad, for example silicone gel or any suitable gel. The gel pad 196 may be utilized to provide therapeutic benefits, such as heating or cooling. Alternatively, a bladder 196 may be used in place of the gel pad. The bladder may be closed and formed of materials that will expand very little to define a single size. An inflatable or expandable bladder may also be used. The bladder may be filled with any suitable fluid, such as water or air, in order to define a particular size pad. Different size pads or bladders, or the expandable bladder, may be provided to alter the amount of dorsiflexion provided by the dorsal splint 100.

As shown in FIG. 16, the substantially rigid splint member 110 includes lower wing portions 132 along the edges of the lower portion 134 of the substantially rigid splint member 110. At least one slot 134 is provided in each of the lower wing portions 132 for receiving strap ends in a manner previously discussed. The lower wing portions 132 may be provided with living hinges in a similar manner as discussed above. As also discussed above, the overmold 138 encases an outer edge of the lower portion 124 of the substantially rigid splint member 110 and further encompasses the slots 134 in the lower wing portions 132. This configuration provides the benefits, as discussed above, of a better and more comfortable fit for the dorsal splint 100.

A distal strap 170 is provided for engaging the slots 134 in the lower portion 124 of the substantially rigid splint member 110. In order to adjust the angle of dorsiflexion, a plurality of interchangeable straps may be provided having different thicknesses. For example, the portion of the strap 170 that contacts the plantar surface of the foot may have a first thickness, and the edges of the strap that engage the slots may have a second thickness that is less than the first thickness. A second, interchangeable strap may be provided having a third thickness in the portion of the strap that contacts the plantar surface of the foot, while having the same second thickness along the edges. The third thickness may be less than or greater than the first thickness and the second thickness along the edges may be less than the third thickness. In this manner, the dorsiflexion may be adjusted by the use of different straps.

An alternate embodiment of the lower wing portion 132 is shown in FIG. 17A. In this embodiment, two slots 134 are provided in each of the lower wing portions 132, for receiving the ends of a dual strap 190, as shown in FIGS. 17B and 17C. The dual strap 190 has first and second strap portions 192, 194 combined with a connecting portion 195. The first and second strap portions 192, 194 may be formed from an inelastic, non-stretch fabric, such as woven nylon.

The first and second strap portions 192, 194 may each include hook and/or hook receiving material at either end thereof The connecting portion 195 may be formed from a somewhat flexible or stretchy material, such as a urethane foam, or neoprene, or any other suitable material, in order to provide a comfortable fitting surface for the plantar surface or to conform to the convex shape of the plantar surface of the user's foot. The connecting portion 195 may be provided with hook and/or hook receiving material so that the ends of the first and second strap portions 192, 194 may be connected thereto.

Of course, the different features discussed herein may be utilized with any of the previously disclosed embodiments. Specifically, any of the straps utilizing gel pads or bladders may be utilized with any dorsal splint disclosed herein.

O. Detailed Description of Various Strap Embodiments for Use With a Dorsal Splint An embodiment of a hybrid strap 1800 for use with a dorsal splint is shown in FIG. 18.

The hybrid strap 1800 is formed from a layer of flexible material 1810 which may be a thin layer of flexible material such as urethane foam or neoprene. The layer of flexible material 1810 has or defines a first width, which may be uniform or non-uniform.

Strips 1820 of non-stretch material, such as woven nylon having widths that are less than the width of the layer of flexible material 1810 are provide along the length of the layer of flexible material 1810. Thus, the length of the hybrid strap is fixed. In alternative configurations, the non-stretch material can be shorter than stretch material so it only limits the overall stretch of the strap. Also, the materials may have non-linear shapes (half moon, etc.) in order to vary the strap stretch across the width of the strap.

The strips 1820 and the layer of flexible material 1810 are connected together in any suitable manner, such as by sewing or adhesive. The strips 1820 may aligned along the edges of the layer of flexible material 1810, or offset from the edges. In this manner the lengthwise stretch of the strap is limited, and the length of the strap is fixed.

The width of the strap 1800 is varied by the flexibility of the layer of flexible material 1810. Thus a more comfortable strap is provided that maintains the splint in position on the foot or calf with a consistent strength, due to the fixed strap length, is provided.

Hook and/or loop material is provided along the layer of flexible material 1810. Fasteners of hook and/or loop material 1830 are provided along the width at each end of the layer of flexible material 1810. The fasteners may also be of non-stretch material, so that the ends of the strap 1800 may be easily passed through slotted portions in the dorsal splint.

The strap 1800 may be utilized in any of the embodiments of a dorsal splint discussed herein.

An alternate configuration of a strap 170 is shown in FIG. 19, as previously mentioned. The strap 170 may be a thermoformed padding strap. The strap 170 includes foam 176, non-stretch unbroken loop material 174 on one side, and stretch material 180 on the other side where a pattern is formed. The thermoformed side 180 is positioned against the skin, thus providing cushioning. In this way, the strap 170 has a defined and limited length; however, the cushioning of the foam 176 allows conformity of the strap 170 against the foot. Holes may be strategically placed (where the pad thickness is completely knocked down) on the thermoformed area to provide breathability.

A further embodiment of a distal strap assembly 2060 for use with a dorsal splint 2000 is shown in FIGS. 20A-C. In this configuration, a flexible edge overmold 2038 extends around and encompasses the periphery of the dorsal splint 2000. Slots 2034 in the lower portion of the dorsal splint 2000 provide attachment points for straps 2070 of the strap assembly 2060.

The strap assembly 2060 also includes a distal bottom piece 2080 that has a width W that is as large as the average male's foot for preventing Morton's neuroma, a noncancerous (benign) growth of nerve tissue that can develop in a nerve of the foot, often between the third and fourth toes. The condition involves a thickening of the tissue around one of the digital nerves leading to the toes.

The distal bottom piece 2080 includes two outer layers 2082 of soft material that are secured to each other at least around two or three edges in order to form a pocket or pouch 2086 therebetween. A cushion or foam layer 2084 is also provided within the pouch 2086 towards the proximal outer layer 2082. The cushion layer 2084 is secured at its edges to at least one of the outer layers 2082.

At least one substantially rigid stay or insert 2090 may be inserted into the pouch 2086 in order to provide structural support to the distal bottom piece 2080 and the plantar surface of the foot, as shown in FIG. 20B. The stay or insert 2090 may be made from any of the above mentioned materials. As shown in FIG. 20C in an alternate configuration, two stays or inserts 2090 are provided into the pouch 2086, which may separate the two stays or inserts 2090 via a seam 2092 that extends the length of the distal bottom piece 2080. In a further variation, the insert 2090 may be cut down the middle in order to reduce the size of the packaging required for the dorsal splint 2000.

Attachment points in the form of D-rings 2088 are provided along the sides of the distal bottom piece 2080 for engagement with the straps 2070. As best seen in FIG. 20B, one end of each strap 2070 engages a respective slot 2034 in the dorsal splint 2000 and the straps 2070 pass through a respective D-ring 2088. The other ends of the straps 2070 wrap around the proximal surface of the lower portion of the dorsal splint 2000. The straps 2070 may thus engage each other to complete the attachment. Alternatively, patches of hook or hook receiving material, such as those shown in FIG. 2A may be provided on or embedded in the proximal surface of the lower portion of the dorsal splint 2000 so the other ends of the straps 2070 may be anchored thereto.

As previously mentioned, the insert piece 2090 can be removable depending on the user's need. Alternatively, the insert piece 2090 or pieces may be retained in the pocket or pouch 2086 in a manner similar to those previously discussed.

P. Detailed Description of an Embodiment of a Dorsal Splint

In observing FIGS. 21A-21C, another embodiment of a splint member 2100 is shown. According to this embodiment, the splint member 2100 includes many of the features belonging to other embodiments described herein including upper and lower portions 2123, 2125, a substantially rigid intermediate portion 2102 surrounded by an edge overmold 2104 and living hinges 2108. These features may be similar to those described in connection with the basic embodiment of FIGS. 1A-1E.

The splint member 2100, in a variation of other embodiments described herein, includes an aluminum stay 2106 (depicted by dashed lines) which is preferably embedded or encased within the intermediate portion 2102. The aluminum stay 2106 is preferably bendable at bend area 2118 along with the intermediate portion 2102 in order to custom-fit or modify the therapeutic angle of the splint member 2100. However, when worn on a leg, the stay 2106 effectively retains its bent shape so as to maintain its shape and the shape of the intermediate portion 2102. It is only when the splint member 2100 is not in use or being worn that one may modify the shape of the splint member 2100.

As depicted in FIG. 21D, the splint member 2100, by way of the stay 2106, may be bent from an original splint member shape 2128A to a modified splint member shape, as exemplified by 2128B. The splint member 2100 generally bends at or around the bend area 2118, as shown in FIG. 21A.

The intermediate portion 2102 defines a plurality of locating apertures 2124 which reveal the location of the stay 2106 located within the intermediate portion 2102. The intermediate portion 2102 defines a recessed portion 2119 located around the bend area 2118 which facilitates and indicates the bending of the stay 2106. Other apertures may be located on the intermediate portion to further reveal the stay 2106 and to reduce weight of the intermediate portion 2102.

The intermediate portion 2102 defines along its length an upper neck 2103 and a lower neck 2105, and a bulbous width portion 2107. The upper and lower necks 2103, 2105 reduce the material of the width of the intermediate portion 2102 and minimize extension of the rigid splint material over the foot and ankle. As a result of the upper and lower necks 2103, 2105, the edge overmold 2104 defines flap portions 2109, 2111 defined by larger portions of material defining the edge overmold thereby providing greater cushioning along the foot and ankle corresponding to such flap portions.

The edge overmold therefore has sections of greater size, defined by length, width or thickness, located along the length of the rigid splint member. The overmold edge sections may be tailored in size according to locations of the foot and ankle to provide increased of cushioning.

Additionally, the intermediate portion 2102 forms an opening 2110 which corresponds to an opening 2130 formed within the stay 2106. These corresponding openings 2110, 2130 allow for one to identify if the stay 2106 is properly aligned with the intermediate portion 2102. A recessed portion 2114 is located on the bulbous portion 2107 and surrounds the opening 2110, and allows for the location of a fastener material, such as a loop fabric, to be inserted therein. The geometry of the bulbous portion 2107 provides a greater area to secure fastener material and corresponding straps.

Turning to the posterior of the splint member 2100, while it is preferable that the stay 2106 is embedded within the intermediate portion 2102, it is evident from FIGS. 21B and 21C that the stay 2106 may slightly bulge along lines 2122 of the intermediate portion 2102. Further, cross-tabs 2120 may be molded or applied to the posterior side of the intermediate portion 2102 for the location of a fastener material, such as a hook fabric to be inserted therein.

Another feature of the embodiment of FIGS. 21A-21B is the provision of venting through slots 2116, 2126. These slots 2116, 2126 are particularly advantageous when strapping is provided with the splint member 2100 so as to allow for adequate ventilation through the straps and the splint member. The slots further reduce material of the intermediate portion, and may be combined with recesses 2112 so as to minimize the weight of the splint member. The slots or recesses may be provided at a plurality of locations of the splint member and are not limited to the arrangement shown herein. As for the holes 2116, these are provided to locate and stabilize the stay 2106 in place during the molding process. The recesses 2112 may extend through the entirety of the splint member 2100 so as to allow for better breathability, as in the slots 2116, 2126, may be provided to reduce weight of the splint member 2100, or can be provided for ornamental purposes.

Q. Detailed Description of Another Strap System for Use With a Dorsal Splint

FIGS. 22A-22D exemplify a strap system 2200 which may be used in combination with embodiments of splint members 2202 described herein. This strap system 2200 is provided to snugly secure the splint member 2202 to the foot, ankle and calf portions of the wearer. Padding is provided along with the strapping to more comfortably and stably connect the splint member to the wearer.

The strap system 2200 includes an ankle portion 2204 and a toe and plantar portion 2206 which are connected by a bridge portion 2208. A calf portion 2210 extends from the ankle portion 2204. An interior padding liner 2224 may be secured to the posterior surface of the splint member 2202 so as to cushion the foot and leg when the strap system 2200 tightens the splint member 2202 against the foot and leg. The interior padding may be of any type described herein, such as a thermoformed padding having localized areas of different degrees of compressibility corresponding to different parts of the foot, ankle and leg, or a continuous padding having generally uniform compressibility and consistent thickness.

The ankle portion 2204 includes a heel stirrup 2222 which secures the strap system 2200 to the heel and under the foot. The ankle portion 2204 includes opposed straps 2225, 2226 that secure opposed ends of the ankle portion 2204 over the anterior surface of the splint member. The ankle portion 2204 also includes generally stretchable straps 2231, 2233 connecting to the padding liner 2224 and the straps 2225, 2226. The stretchable straps 2231, 2233 permit adjustment of the straps 2225, 2226 to the splint member, and also further retain the splint member on the ankle when the straps 2225, 2226 are adjusted.

The splint member may define a recessed portion, as in the recess 2114 in FIG. 21A, which accommodates a hook and loop material and secures to corresponding hook and loop material on the strap 2226. A strap locator 2234 may be located on the splint member 2202 to retain the straps in a position relative to the splint member 2202 (i.e., the splint member may be formed from plastic upon which the straps may slide).

The calf portion 2210 includes opposed tabs 2215, 2216 securing to slots 2230 which are formed on the splint member 2202. The tabs 2215, 2216 and locations on the calf portion 2210 fasten to one another via fasteners, such as with corresponding hook and loop material.

The ankle portion 2204 connects to the toe portion 2206 via the bridge portion 2208. The bridge portion 2208 may be formed from a stretchable material so as to accommodate movement of different portions of the leg and foot and different foot sizes. Alternatively, the bridge portion 2208 may be substantially non-stretchable so as to maintain the ankle and toe portions 2204, 2206 in close-relationship. The selection of the bridge portion material thus will depend on the activity of the wearer and the intended treatment served by the splint member and the strap system.

Turning to the toe portion 2206, this secures to the splint member 2202 via a sleeve 2211 fitted to closely conform to the corresponding toe portion of the splint member 2202. An edging 2232 extending from the sleeve 2211 wraps about peripheral edge portions of the splint member 2202 into portions corresponding to the ankle portion 2204 and calf portion 2210 of the strap system 2200. The interior side of the sleeve 2211 forms part of the inner padding liner 2224 and the edging 2232 likewise forms part of or connects to the interior padding liner 2224. The sleeve 2211 and the edging 2232 may be secured to the splint member 2202 by suitable fasteners such as hook and loop material.

The toe portion 2206 includes an angled pull defined by stitching or divider 2227 which joins two opposing ends 2221, 2223 of each of corresponding straps 2212, 2214. By pulling on the straps 2212, 2214 to join the straps to one another, the straps wrap around the prominent bony area of the foot (head of the metatarsal joints) comfortably from opposite directions so as to conform to the toe region of the foot. Suitable fastener systems of types described herein and known to the skilled artisan may be used to secure the straps 2212, 2214 to one another.

The toe portion 2206 also includes a plantar pad 2228. This plantar pad 2228 may be formed from a high density foam or rigid plastic sheet placed along the plantar portion of the toe portion 2206 where the metatarsals will be when the splint member worn. Portions of the plantar pad 2229 may comprise island pads that have increased areas of compressibility or are distinguished from other areas on the basis of surface area or other geometry in order to accommodate the corresponding region of the foot. As with similar embodiments described herein, the plantar pad is included to provide rigidity to avoid pressure points on the heads of the metatarsal joints so as to prevent Morton's neuroma.

The toe portion 2206 further includes openings 2218 formed on both straps 2212, 2214 so as to provide pressure relief on the side of the foot when the strap system 2200 is tightly secured to the leg and foot. This pressure relief on the side of the foot also assists in preventing Morton's neuroma.

Lastly, the toe portion 2206 includes a toe stopper 2220 connecting or securable to the front end of the sleeve 2211 and the inner padding liner 2224. Further, the toe stopper 2220 provides a visual guide for proper application of the splint member to the foot. The splint member is found to be more functional when the bottom end of the splint member is placed close to the end of the foot. The toe stopper 2220 visually guides the wearer to maintain the toes from passing through or inadequately approaching the end of the splint member during application. Additionally, the toe stopper 2220 is positioned to maintain the angle of the flexion of the foot by maintaining better contact with the shell and foot.

The strapping system 2200 may be formed in the manner of any of the other strap embodiments described herein, and is not limited to the padding and individual straps shown herein.

R. Conclusion

The disclosed embodiments of a dorsal splint and straps for use with a dorsal splint provide great flexibility for dorsal splints having better and more comfortable fit, improved ability to hold a functional angle of the foot in flexion for optimum therapeutic value, and for dorsal splints that may have lower profiles for retail display, storage, and traveling.

It is understood that the size of the dorsal splint and the components thereof can be adjusted so that different users having different sized legs, ankles, and feet may benefit from the present design. Specifically, the width, thickness and length of the splint member may be varied to accommodate different sized users. Of course, many of the improvements disclosed herein, such as the overmold and the living hinge, allow a single size dorsal splint to comfortably fit a larger number of different sized users.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments. In addition to the variations described herein, other known equivalents for each feature can be mixed and matched by one of ordinary skill in this art to construct a dorsal splint in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof Thus, it is intended that the scope of the present invention herein disclosed should not be limited by the particular disclosed embodiments described above.

The invention claimed is:

1. An orthopedic device, comprising:
   a splint member being substantially rigid and formed from a thermoplastic or thermosetting polymer, the splint member defining anterior and posterior surfaces, the splint member having an original shape wherein the splint member defines along a length of the splint member an upper portion, an intermediate portion and a lower portion, and in the original shape the posterior surface of the splint member has a concave shape along the length of the splint member and at least in the intermediate and upper portions, and the splint member has rigid edges which are hard;
   an edge overmold being flexible and integrally secured along at least a portion of the rigid edges of the splint member, the edge overmold extending outwardly from the periphery of the splint member and having greater flexibility than the splint member;
   a stay being formed from a bendable aluminum metal embedded in the splint member between the anterior and posterior surfaces and within the intermediate portion of the splint member, the stay arranged to maintain a shape when the orthopedic device is worn by a wearer, and wherein the stay is bendable to place the splint member into a modified shape different from the original shape;
   wherein the splint member and the stay form a bend area located only within the intermediate portion of the splint member such that the stay is bendable at the bend area in order to custom-fit or modify a therapeutic angle of the splint member within the intermediate portion by arranging the upper and lower portions relative to one another;
   wherein the original shape defines an original angle of the upper portion relative to the lower portion along the length within the range of 80° to 90°, and the therapeutic angle is defined as being the same as or different from the original angle and within the range of 80° to 90°.

2. The orthopedic device according to claim 1, wherein the intermediate portion defines an upper neck and a lower neck, and a bulbous width portion located between the upper and lower necks which each reduce material of the width of the intermediate portion relative to the bulbous width portion, the bulbous width portion generally corresponding to the bend area and symmetrically extends outwardly in width within first and second sides delimited by the rigid edges of the intermediate portion.

3. The orthopedic device according to claim 2, wherein the edge overmold forms flaps on opposed sides along peripheries of the upper and lower necks having a larger portions than at the bulbous width portion.

4. The orthopedic device according to claim 1, wherein the splint member defines a recessed portion located around the bend area and arranged for facilitating bending of the stay, wherein the recessed portion is defined along the anterior surface of the splint member between rigid edges of the intermediate portion.

5. The orthopedic device according to claim 1, wherein a shape configuration of the lower portion remaining substantially the same as the stay is bent.

6. The orthopedic device according to claim 1, wherein the stay is more rigid than the splint member.

7. The orthopedic device according to claim 1, wherein the orthopedic device includes at least one opening extending through a thickness of the splint member and the stay.

8. The orthopedic device according to claim 1, wherein the stay continuously extends along a length and through the upper, intermediate and lower portions of the splint member.

9. The orthopedic device according to claim 1, wherein the stay slightly bulges along lines formed by the intermediate portion and along the posterior surface of the orthopedic device within the concave shape.

10. An orthopedic device, comprising:
a splint member being substantially rigid and formed from a thermoplastic or thermosetting polymer, the splint member defining anterior and posterior surfaces, and peripheral surfaces, the splint member having an original shape wherein the splint member defines along a length of the splint member an upper portion, an intermediate portion and a lower portion, and in the original shape the posterior surface of the splint member has a concave shape and at least in the intermediate and upper portions along the length of the splint member, and the splint member has rigid edges which are hard;
a stay being bendable aluminum metal embedded in the splint member between the anterior and posterior surfaces and within the intermediate portion of the splint member, the stay arranged to maintain a shape when the orthopedic device is worn by a wearer, and wherein the stay is bendable to place the splint member into a modified shape different from the original shape;
wherein the splint member and the stay collectively form a bend area located only within the intermediate portion of the splint member such that the stay is bendable at the bend area in order to custom-fit or modify a therapeutic angle of the splint member within the intermediate portion by arranging the upper and lower portions relative to one another;
wherein the original shape defines an original angle of the upper portion relative to the lower portion along the length within the range of 80° to 90°, and the therapeutic angle is defined as being the same as or different from the original angle and within the range of 80° to 90°.

11. The orthopedic device according to claim 10, wherein the lower portion defines a flared distal end portion.

12. The orthopedic device according to claim 11, wherein the lower portion defines venting through slots extending through the entirety of the splint member.

13. The orthopedic device according to claim 10, wherein the stay slightly bulges along lines formed by the intermediate portion and along the posterior surface of the orthopedic device within the concave shape.

14. The orthopedic device according to claim 10, wherein the intermediate portion defines an upper neck and a lower neck, and a bulbous width portion located between the upper and lower necks which each reduce material of the width of the intermediate portion relative to the bulbous width portion, the bulbous width portion generally corresponding to the bend area and symmetrically extends outwardly in width within first and second sides delimited by the rigid edges of the intermediate portion.

15. An orthopedic device, comprising:
a splint member being substantially rigid and formed from a thermoplastic or thermosetting polymer, the splint member defining anterior and posterior surfaces, the splint member having an original shape, wherein the splint member defines along a length of the splint member an upper portion, an intermediate portion and a lower portion, and in the original shape the posterior surface of the splint member has a concave shape, and the splint member has rigid edges which are hard;
an edge overmold being flexible and integrally secured along at least a portion of the rigid edges of the splint member, the edge overmold extending outwardly from the periphery of the splint member and having greater flexibility than the splint member;
a stay being formed from a bendable aluminum metal embedded in the splint member between the anterior and posterior surfaces and within the intermediate portion of the splint member, the stay arranged to maintain a shape when the orthopedic device is worn by a wearer, and wherein the stay is bendable to place the splint member into a modified shape different from the original shape;
wherein the edge overmold extends along the hard and rigid edges at the upper and intermediate portions of the splint member, the lower portion defines a flared distal end portion devoid of the edge overmold.

* * * * *